US011959125B2

(12) United States Patent
Jain

(10) Patent No.: US 11,959,125 B2
(45) Date of Patent: Apr. 16, 2024

(54) UNIVERSAL METHOD FOR EXTRACTING NUCLEIC ACID MOLECULES FROM A DIVERSE POPULATION OF ONE OR MORE TYPES OF MICROBES IN A SAMPLE

(71) Applicant: Sun Genomics, Inc., San Diego, CA (US)

(72) Inventor: Suneer Jain, San Diego, CA (US)

(73) Assignee: Sun Genomics, Inc., San Diego, CA (US)

( * ) Notice: Subject to any disclaimer, the term of this patent is extended or adjusted under 35 U.S.C. 154(b) by 0 days.

(21) Appl. No.: 16/373,387

(22) Filed: Apr. 2, 2019

(65) Prior Publication Data

US 2019/0292584 A1 Sep. 26, 2019

Related U.S. Application Data

(60) Continuation-in-part of application No. 16/042,831, filed on Jul. 23, 2018, now Pat. No. 10,837,046, which is a division of application No. 15/824,754, filed on Nov. 28, 2017, now Pat. No. 10,428,370, which is a continuation of application No. PCT/US2017/051849, filed on Sep. 15, 2017.

(60) Provisional application No. 62/651,620, filed on Apr. 2, 2018, provisional application No. 62/412,787, filed on Oct. 25, 2016, provisional application No. 62/395,316, filed on Sep. 15, 2016.

(51) Int. Cl.
| | |
|---|---|
| *C12Q 1/6806* | (2018.01) |
| *A61K 35/00* | (2006.01) |
| *A61K 35/741* | (2015.01) |
| *C12Q 1/6827* | (2018.01) |
| *C12Q 1/686* | (2018.01) |
| *C12Q 1/689* | (2018.01) |
| *G16B 20/00* | (2019.01) |

(52) U.S. Cl.
CPC .......... *C12Q 1/6806* (2013.01); *A61K 35/741* (2013.01); *C12Q 1/6827* (2013.01); *C12Q 1/686* (2013.01); *G16B 20/00* (2019.02); *A61K 2035/115* (2013.01); *C12Q 1/689* (2013.01)

(58) Field of Classification Search
CPC .......................... C12Q 1/6806; C12N 15/1003
See application file for complete search history.

(56) References Cited

U.S. PATENT DOCUMENTS

| | | | |
|---|---|---|---|
| 4,652,517 A | 3/1987 | Scholl | |
| 4,652,630 A | 3/1987 | Bentle | |
| 4,900,677 A | 2/1990 | Hewitt | |
| 5,075,430 A | 12/1991 | Little | |
| 5,155,018 A | 10/1992 | Gillespie | |
| 5,223,402 A | 6/1993 | Abbas | |
| 5,234,809 A | 8/1993 | Boom | |
| 5,350,679 A | 9/1994 | Hess | |
| 5,595,876 A | 1/1997 | Rakestraw | |
| 5,928,875 A | 7/1999 | Breen et al. | |
| 6,180,778 B1* | 1/2001 | Bastian | C12N 15/1006 536/25.3 |
| 7,683,035 B1 | 3/2010 | Erbacher | |
| 9,463,208 B2 | 10/2016 | Hlavaka | |
| 9,598,721 B2 | 3/2017 | Klein | |
| 9,827,264 B1 | 11/2017 | Palumbo | |
| 10,428,370 B2* | 10/2019 | Jain | C12Q 1/6827 |
| 10,760,065 B2* | 9/2020 | Lu | C12N 9/22 |
| 10,837,046 B2* | 11/2020 | Jain | A61K 35/741 |
| 2001/0043916 A1 | 11/2001 | McNeilly | |
| 2002/0001829 A1 | 1/2002 | Lee et al. | |
| 2002/0010145 A1* | 1/2002 | Willson, III | C12N 15/1003 514/44 R |
| 2003/0096429 A1 | 5/2003 | Baeunnner | |
| 2004/0072242 A1 | 4/2004 | Hunter | |
| 2004/0076990 A1 | 4/2004 | Picard | |
| 2005/0164260 A1 | 7/2005 | Chen | |
| 2006/0173165 A1 | 8/2006 | Falson et al. | |
| 2006/0204978 A1* | 9/2006 | Nilsen | C12Q 1/689 435/6.11 |

(Continued)

FOREIGN PATENT DOCUMENTS

| | | |
|---|---|---|
| AU | 3995195 | 6/1996 |
| CN | 1307644 A | 8/2001 |

(Continued)

OTHER PUBLICATIONS

Buffer ASL, Qiagen Safety Data Sheet ( Aug. 2017) (Year: 2021).*
Casen et al.,Deviations in human gut microbiota: a novel diagnostic test for determining dysbiosis in patients with IBS or IBD. Alimentary Pharmacology and Therapeutics 42 : 71-83 (Year: 2015).*
Claesson et al.,Gut microbiota composition correlates with diet and health in the elderly. Nature 488:178 (Year: 2012).*
David et al.,Host lifestyle affects human microbiota on daily timescales. Genome Biology 15:R89 (Year: 2014).*
David et al., Diet rapidly and reproducibly alters the human gut microbiome. Naturew 505: 559 (Year: 2014).*
Davis et al., A dose dependent impact of prebiotic galactooligosaccharides on the intestinal microbiota of healthy adults. Intl. J. of Food Microbiology 144 : 285 (Year: 2010).*

(Continued)

*Primary Examiner* — Ethan C Whisenant
(74) *Attorney, Agent, or Firm* — DLA Piper LLP (US)

(57) ABSTRACT

Disclosed herein are methods of extracting genetic material from a diverse population of one or more types of microbes in a sample. Microbes can be prokaryotes or eukaryotes and may include bacteria, archaea, fungi, protozoa, helminths, parasites, viruses, phages, and others. Extraction may be from a single sample and subsequent identification may be through a molecular method such as qPCR, PCR, RFLP, SSCP, allele specific PCR, targeted sequencing, pull down sequencing, whole shotgun sequencing, or other methods. Also provided are methods that include extracting nucleic acid molecules from a variety of organisms such as fungi (i.e., *Saccharomyces* spp.), animal cells (*Bos taurus*), plants (e.g., *Hordeum vulgare*) from the gut of a human subject, performing a metagenomics analysis therefrom, and determining a probiotic treatment or dietary guidance for the subject based on the metagenomics analysis.

17 Claims, 22 Drawing Sheets

(56) References Cited

U.S. PATENT DOCUMENTS

| | | |
|---|---|---|
| 2007/0015139 A1 | 1/2007 | Gayral |
| 2007/0015177 A1* | 1/2007 | Maron .............. C12N 15/1003 435/6.16 |
| 2007/0280923 A1 | 12/2007 | Kerner |
| 2008/0003564 A1 | 1/2008 | Chen |
| 2008/0014578 A1 | 1/2008 | Horikoshi |
| 2008/0199863 A1 | 8/2008 | Haake |
| 2008/0264842 A1 | 10/2008 | Hukari |
| 2009/0109057 A1* | 4/2009 | Lenger ................... H04Q 9/00 340/870.07 |
| 2010/0196894 A1* | 8/2010 | Buelte .................. C12Q 1/689 435/6.15 |
| 2011/0091431 A1 | 4/2011 | Olmstead |
| 2011/0130558 A1 | 6/2011 | Ritt |
| 2011/0200983 A1* | 8/2011 | Smith ................... C12Q 1/701 435/5 |
| 2012/0021421 A1* | 1/2012 | Amar ................... C12Q 1/6888 435/6.12 |
| 2012/0046178 A1* | 2/2012 | Van Den Boom ... C12Q 1/6853 506/4 |
| 2012/0130061 A1* | 5/2012 | Himmelreich ..... C12N 15/1003 536/25.41 |
| 2012/0165215 A1* | 6/2012 | Andersen ............ C12Q 1/6837 506/9 |
| 2012/0196283 A1* | 8/2012 | Babiel .................. C12P 19/34 435/6.11 |
| 2012/0207726 A1 | 8/2012 | Lipkin et al. |
| 2013/0065790 A1 | 3/2013 | Vos |
| 2013/0079251 A1 | 3/2013 | Boles |
| 2013/0109027 A1 | 5/2013 | Kiss |
| 2013/0121968 A1* | 5/2013 | Quay .................... C12Q 1/689 424/93.4 |
| 2013/0165635 A1 | 6/2013 | Kim |
| 2013/0338350 A1 | 12/2013 | Hurt et al. |
| 2014/0147425 A1 | 5/2014 | Henn et al. |
| 2014/0200149 A1* | 7/2014 | Andersen ............... C12Q 1/689 506/9 |
| 2014/0212868 A1 | 7/2014 | Wilmes et al. |
| 2014/0271557 A1* | 9/2014 | Lee ........................ C12Q 1/689 424/93.4 |
| 2015/0044687 A1* | 2/2015 | Schmitt ............... C12Q 1/6876 435/6.12 |
| 2015/0050293 A1* | 2/2015 | Ley ......................... A61K 39/40 424/164.1 |
| 2015/0079601 A1 | 3/2015 | Slepnev |
| 2015/0225712 A1 | 8/2015 | Gunther et al. |
| 2015/0240290 A1 | 8/2015 | Gosiewski |
| 2015/0322176 A1 | 11/2015 | Monteiro |
| 2015/0355178 A1 | 12/2015 | Myatt |
| 2015/0366941 A1 | 12/2015 | Menear et al. |
| 2015/0374760 A1* | 12/2015 | Scher ...................... A61K 35/74 424/93.3 |
| 2016/0030494 A1 | 2/2016 | Henn |
| 2016/0074435 A1 | 3/2016 | Huang et al. |
| 2016/0114322 A1* | 4/2016 | Ismagilov ........... B01F 13/0083 506/9 |
| 2016/0115471 A1 | 4/2016 | Kim |
| 2016/0129053 A1 | 5/2016 | Brass et al. |
| 2016/0143961 A1* | 5/2016 | Berry ...................... A61P 43/00 424/93.3 |
| 2016/0271189 A1 | 9/2016 | Cutcliffe et al. |
| 2017/0044595 A1 | 2/2017 | Fischer et al. |
| 2017/0114396 A1 | 4/2017 | Chim et al. |
| 2017/0138941 A1 | 5/2017 | Cao |
| 2017/0151268 A1* | 6/2017 | von Maltzahn .... A61K 31/7034 |
| 2017/0312321 A1 | 11/2017 | Nistal et al. |
| 2017/0343455 A1 | 11/2017 | Middleton |
| 2017/0360848 A1 | 12/2017 | Adams et al. |
| 2017/0368143 A1* | 12/2017 | Petri, Jr. .............. A61K 31/4164 |
| 2018/0002741 A1 | 1/2018 | Finegold et al. |
| 2018/0050070 A1 | 2/2018 | Finlay et al. |
| 2018/0066291 A1 | 3/2018 | Berekaa |
| 2018/0071344 A1 | 3/2018 | Berry |
| 2018/0080065 A1 | 3/2018 | Jain |
| 2018/0102187 A1 | 4/2018 | Apte et al. |
| 2018/0187181 A1 | 7/2018 | Driscoll |
| 2018/0268048 A1* | 9/2018 | Haiminen .............. G16B 20/00 |
| 2019/0060390 A1* | 2/2019 | Paufique ............. A61K 36/8968 |
| 2019/0224230 A1* | 7/2019 | McLaren .............. A23L 29/212 |
| 2019/0247447 A1* | 8/2019 | Button ................. A61K 35/741 |
| 2019/0256583 A1* | 8/2019 | Goepp ................. A61K 35/741 |
| 2020/0330529 A1* | 10/2020 | Ravel ....................... C12N 1/20 |
| 2020/0405777 A1* | 12/2020 | Khan ..................... A61P 43/00 |
| 2021/0260139 A1 | 8/2021 | Elinav et al. |
| 2022/0064730 A1* | 3/2022 | Dor ...................... C12Q 1/6883 |

FOREIGN PATENT DOCUMENTS

| | | | |
|---|---|---|---|
| CN | 101801200 | 10/2014 | |
| CN | 108135944 | 6/2018 | |
| EP | 1082455 | 3/2001 | |
| EP | 2739394 | 6/2014 | |
| JP | S61-195698 | 8/1986 | |
| JP | H09-47290 | 2/1997 | |
| JP | H09-508638 | 9/1997 | |
| JP | 2002-516668 | 6/2002 | |
| JP | 2002-541824 A | 12/2002 | |
| JP | 2014-521354 | 8/2014 | |
| WO | WO 1996/017933 | 6/1996 | |
| WO | WO 1999/061667 | 12/1999 | |
| WO | WO 2002/007741 A1 | 1/2002 | |
| WO | WO-2010002890 A2 * | 1/2010 | ........... C12Q 1/6883 |
| WO | WO 2012/043183 A1 | 4/2012 | |
| WO | WO 2012/159023 A2 | 11/2012 | |
| WO | WO 2013/020089 | 2/2013 | |
| WO | WO 2013/068107 | 5/2013 | |
| WO | WO 2014/188378 A1 | 11/2014 | |
| WO | WO 2015/013214 A2 | 1/2015 | |
| WO | WO 2016/124642 A1 | 8/2016 | |
| WO | WO 2017/044880 A1 | 3/2017 | |
| WO | WO 2017/070123 A1 | 4/2017 | |
| WO | WO 2018/136884 A1 | 7/2018 | |

OTHER PUBLICATIONS

Ezendam et al., Probiotics: Immunomodulation and Evaluation of Safety and Efficacy. Nutrition Reviews 64(1) : 1-14 (Year: 2006).*
Kassam et al., Am. J of Gastroenterology 108 :500 (Year: 2013).*
Ojima et al., Metagenomic Analysis Reveals Dynamic Changes of Whole Gut Microbiota in the Acute Phase of Intensive Care Unit Patients. Dig. Dis Sci. 61:1628-1634 (Year: 2012).*
Patel et al., New Approaches for Bacteriotherapy: Prebiotics, New-Generation Probiotics, and Synbiotics. Clinical Infectious Diseases 60(S2) S108-121 (Year: 2015).*
Prinvipi et al., Antibiotic administration and the development of obesity in children. Intl. J. of Antimicrobial Agents 47 (3) :171-177 (Year: 2016).*
Schrezenmeir et al., Probiotics, prebiotics, and synbiotics—approaching a definition. Am. J. of Clin Nutr. 73(suppl) :361S-4S (Year: 2001).*
Shin et al.,Proteobacteria: microbial signature of dysbiosis in gut microbiota. Trends in Biotechnology 33(9) 496 (Year: 2015).*
Tringe et al., Comparative Metagenomics of Microbial Communities. Science 308 :554 (Year: 2005).*
Turnbaugh et al., The Effect of Diet on the Human Gut Microbiome: A Metagenomic Analysis in Humanized Gnotobiotic Mice. Science Translational Medicine 1(6) : 1 (Year: 2009).*
Vernocchi et al., Gut Microbiota Profiling: Metabolomics Based Approach to Unravel Compounds Affecting Human Health. Frontiers in Microbiology 7 :1144 (Jul. 2016).*
Wischmeyer et al., Role of the microbiome, probiotics, and 'dysbiosis therapy' in critical illness. Curr Opin Crit Care 22: 347-353 (Year: 2016).*
Wolf, N., Treating Dysbiosis Natural Partners blog (Year: 2015).*
Zaborin et al., Membership and Behavior of Ultra-Low-Diversity Pathogen Communities Present in the Gut of Humans during Prolonged Critical Illness. mBio 5(5) : e01361-14 (Year: 2014).*

(56) References Cited

OTHER PUBLICATIONS

Zhou et al., DNA Recovery from Soils of Diverse Composition. Applied and Environmental Microbiology 62(2) : 316-322 (Year: 1996).*
Allali et al., A comparison of sequencing platforms and bioinformatics pipelines for compositional analysis of the gut microbiome. BMC Microbiology 17: 194 (Sep. 13, 2017) (Year: 2017).*
Bokulich et al., Quality-filtering vastly improves diversity estimates from Illumina amplicon sequencing. Nature Methods 10(1) : 57 (Year: 2013).*
Lee et al., A community-based study of Helicobacter pylori Therapy using the Strategy of Test, Treat, Retest and Re-treat Initial Treatment Failures. Helicobacter 11: 418-424 (Year: 2006).*
Lim et al., Clinical Insights from Metagenomic Analysis of Sputum Samples from Patients with Cystic Fibrosis. J. of Clinical Microbiology 52(2) : 425-437 (Year: 2014).*
Qin et al., A human gut microbial gene catalogue established by metagenomic sequencing. Nature 464: 59-67 (Year: 2010).*
RNAqueous Kit Protocol (Year: 2008).*
Wood et al., Kraken :ultrafast metagenomic sequence classification using exact alignments. Genome Biology 15 : R46(12pgs) (Year: 2014).*
Crew, Lieu.Clinical guidelines on the identification , evaluation, and treatment of overweight and obesity in adults. Academia (Apr. 2007). (Year: 2007).*
Lozupone et al., UniFrac: an effective distance metric for microbial community comparison. The ISME J. 5:169-172 (Year: 2011).*
Thoendel et al., Comparison of microbial DNA enrichment tools for metagenomic whole genome sequencing. J. of Microbiological Methods 127:141-145 (May 2016) (Year: 2016).*
Kwong et al., Pathology 47(3) : 199-210 (Year: 2015).*
Brumfield et al., PLOS One 0228899 (Feb. 13) (Year: 2020).*
Durazzi et al., Scientific Reports 11 :3030 (Year: 2021).*
Hillman et al., 3(6) :e00069-18 (Nov.) (Year: 2018).*
Schloss et al., Applied and Environmental Microbiology 75(23) : 7537 (Year: 2009).*
Su et al., Bioinformatics 28(19) :2493 (Year: 2012).*
Su et al., Bioinformatics 30(7) : 1031 (Year: 2014).*
Dehoux, Pierre et al.: "*Comparative genomics of Clostridium boltea and Clostridium clostridioforme reveals species-specific genomic properties and numerous putative antibiotic resistance determinants*"; BMC Genomics, Oct. 21, 2016, 17:819, pp. 1-16.
Extended European Search Report dated Mar. 11, 2020, regarding EP 17 85 1634.
Gautam and Sharma: "*Evaluation of Probiotic Potential of New Bacterial Strain, Lactobacillus spicheri G2 Isolated from Gundruk*"; Proc. Natl. Acad. Sci., India, Sect. B Biol. Sci., Oct.-Dec. 2015, 85(4):979-986.
Grund and Ensign: "*Activation of Streptomyces viridochromogenes Spores by detergents*"; Current Microbiology, 7 (1982), pp. 223-228.
International Search Report dated Apr. 7, 2020, regarding PCT/US2019/058224.
Jie, Z. et al.: "*A multi-omic cohort as a reference point for promoting a healthy human gut microbiome*"; BioRxiv, Mar. 24, 2019, pp. 1-49; doi.org/10.1101/585893.
Patel and Dupont: "*New approaches for Bacteriotherapy: Prebiotics, New-Generation Probiotics, and Synbiotics*", Clinical Infectious Disease, 2015:60, (Suppl. 2) S108-S121.
Setlow, Peter: "*Spore Germination*"; Current Opinion in Microbiology, 2003, 6:550-556.
Wei, Jie et al.: "Superdormant Spores of Bacillus Species Germinate Normally with High Pressure, Peptidoglycan Fragments, and Bryostatin"; J. of Bacteriology, Mar. 2010, 192(5), pp. 1455-1458.
Boom et al.: "*Rapid and Simple Method for Purification of Nucleic Acids*"; J. of Clinical Microbiology, 1990, 28(3) : 495.
Cano et al.: "*Revival and Identification of Bacterial spores in 25- to 40-Million-Year-Old Dominican Amber*"; Science, May 1995, vol. 268, pp. 1060-1064.
ConsumerLab.com: "*Some Surprising Results from Tests of 43 probiotic supplements and Kefir drinks*", Nov. 6, 2015, pp. 1-3.
Delzenne et al.: "*Targeting gut microbiota in obesity: effects of prebiotics and probiotics*"; Nat. Rev., Endocrinol., Aug. 9, 2011, pp. 1-8.
Dineen, S. M. et al.: "*An evaluation of commercial DNA extraction kits for the isolation of bacterial spore DNA from soil*";. J. of Applied Microbiology, 2010, 109 : 1886.
Eckberg et al.: "*Diversity of the Human Intestinal Microbial Flora*"; Science, Jun. 10, 2005, vol. 308, pp. 1635-1639.
Erb et al.: "*Detection of polychlorinated biphenyl degradation genes in polluted sediments by direct DNA extraction and polymerase chain reaction*"; Applied and Environmental Microbiology, 1993, 59 (12) : 4065.
Fierer et al.: "*Metagenomic and Small-Subunit rRNA Analyses Reveal the Genetic Diversity of Bacteria, Archaea, Fungi, and Viruses in Soil*", Applied and Environmental Microbiology, 2007, 73 (21) : 7059.
Foster et al.: "*A human gut bacterial genome and culture collection for improved metagenomic analyses*", Nature Biotechnology, 2019, 37, pp. 186-192.
Gill et al.: "*Metagenomic Analysis of the Human Distgal Gut Microbiome*"; Science, vol. 31, Jun. 2, 2006, pp. 1355-1359.
Guarner et al.: "*WGO Guidelines regarding Probiotics and Prebiotics*"; J. of Clinical Gastroenterology, Jul. 2012, 46(6) : 468-481.
Herrick et al.: "*Polymerase Chain Reaction Amplification of Naphthalene-Catabolic and 16S rRNA Gene Sequences from Indigenous Sediment Bacteria*"; Applied and Environmental Microbiology, Mar. 1993, 59 (3) : 687.
Inceoglu et al.: "*Effect of DNA Extraction Method on the Apparent Microbial Diversity of Soil*"; Applied and Environmental Microbiology, May 2010, 76 (10), pp. 3378-3382.
International Search Report dated Jun. 19, 2019, regarding PCT/US2019/025457.
International Search Report dated Jan. 18, 2018, regarding PCT/US2017/051849.
Kuske et al.: "*Small-Scale DNA Sample Preparation Method for Field PCR Detection of Microbial Cells and Spores in Soil*"; Applied and Environmental Microbiology, 1998, 64 (7) : 2463.
Laflamme et al.: "*Flow cytometry analysis of germinating Bacillus spores, using membrane potential dye*"; Arch. Microbiology, 2005, vol. 183, pp. 107-112.
Lemmen et al.: "*Comparison of two sampling methods for the detection of Gram-positive and Gram-negative bacteria in the environment moistened swabs versus Rodac plates*"; Intl. J. of Hygiene and Environmental Health, 2001, 203: 245.
Luo et al.: "*Direct Comparisons of Illumina vs. Roche 454 Sequencing Technologies on the Same Microbial Community DNA Sample*"; Plos One, Feb. 2012, 7(2): e30087, 12 pgs.
Wikipedia: "*Metagenomics*" 2018, entry downloaded Sep. 13, 2018, 18 pgs.
Monsen et al.: "*A general method for cell lysis and preparation of deoxyribonucleic acid from streptococci*"; FEMS Microbiology Letters, 1983, 16 : 19-24.
More et al.: "*Quantitative Cell Lysis of Indigenous Microorganisms and Rapid Extraction of Microbial DNA from Sediment*", Applied and Environmental Microbiology, 1994, 59 (3) : 687.
Mwamburi et al. "*Effect of surfactants and temperature on germination and vegetative growth of Beauveria bassiana*"; Brazilian J. of Microbiology, 2015, 46(1): 67-74.
Protein Solubilization, Jun. 12, 2015, 3 pages; http://www.bio-rad.com/en-us/applications-technologies/protein-solubilization.
Rapley, Ralph: "*Basic Techniques in Molecular Biology*"; Medical Biomethods Handbook, Dec. 27, 2018, Hummana Press, pp. 117.
Sarkosyi (Molecular Biology) Jan. 5, 2015, 2 pages; http://what-when-how.com/molecular-biology/.
Sayler et al.: "*Environmental Application of nucleic acid hybridization*"; Ann. Rev. Microbiol., 1990, 44:625-648.
Schabereiter-Gurtner et al.: "*Evaluation of a protocol for molecular broad-range diagnosis of culture-negative bacterial infections in clinical routine diagnosis*"; J. of Applied Microbiology, 2007, vol. 104, pp. 1228-1237.

(56) References Cited

OTHER PUBLICATIONS

Tebbe et al.: "Interference of Humic Acids and DNA Extracted Directly from Soil in Detection and Transformation of Recombinant DNA from Bacteria and a Yeast"; Applied and Environmental Microbiology, 1993, 59 (8) : 2657.
Tsai and Olson: "Rapid Method for Direct Extraction of DNA from Soil and Sediments", Applied and Environmental Microbiology, Apr. 1991, 57 (4) : 1070.
Tsai and Olson: .Rapid Method for Separation of Bacterial DNA from Humic Substances in Sediments for Polymerase Chain Reaction; Applied and Environmental Microbiology, 1992, 58 (7) : 2292.
Wintzingerode et al.: "Determination of microbial diversity in environmental samples: pitfalls of PCR-based rRNA analysis"; FEMS Microbiology Reviews, 1997, 21 :213-229.
Yuan et al.: "Evaluation of Methods for the Extraction and Purification of DNA from the Human Microbiome"; Plos One, 2012, 7(3) : e33865.
Gill et al., "Metagenomic Analysis of the Human Distal Gut Microbiome", Science, vol., Jun. 2006, 312(5778):1355-1359.
Inceoglu et al., "Effect of DNA Extraction Method on the Apparent Microbial Diversity of Soil", Applied and Environmental Microbiology, May 2010, 76(10):3378-3382.
JP Office Action in Japanese Application No. 2019-515430, dated Jun. 9, 2021 14 pages (with English Translation).
Alby et al., "Homothallic and heterothallic mating in the opportunistic pathogen candida albicans", Nature, Aug. 2009, 460:890-894.
Blinkhorn et al., "Emergence of a New Opportunistic Pathogen, Candida lusitaniae", J. of Clinical Microbiology, 1989, 27(2):236-240.
GenBank Accession No. AY892502, Synthetic construct Homo sapiens clone FLH027852.01L ribonuclease P/IvIRP 30kDa subunit(RPP30) mRNA, partial cds, Jul. 26, 2016 [online].
GenBank Accession No. MT081059, Severe acute respiratory syndrome coronavirus 2 isolate SARS-CoV-2/human/CHN/HS_8/2020 nucleocapsid phosphoprotein (N) gene, complete cds, Apr. 6, 2020 [online].
GenBank Accession No. MT187977, Severe acute respiratory syndrome coronavirus 2 isolate SARS-CoV-2/human/ITA/MBS-Cagliari-1/2020 nucleocapsid phosphoprotein (N) gene, partial cds, Apr. 6, 2020 [online].
Goo et al., "Characterization of novel monoclonal antibodies against MERS-coronavirus spike protein", Virus Research, Jan. 2020, 278:1-11.
Goodman, "The Rise of the Do-It-Yourself Fecal Transplant", WebMD, Dec. 2015, 7 pages.
Hughes et al., "The Gut Microbiota and Dysbiosis in Autism Spectrum Disorders", Clinical Neurology and Neuroscience Reports, Sep. 2018, 18(81):1-15.
Kim et al., "Gut Dysbiosis Promotes M2 Macrophage Polarization and Allergic Airway Inflammation via Fungi-Induced $PGE_2$", Cell Host & Microbe, Jan. 2014, 15:95-102.
Kyne et al., Asymptomatic Carriage of Clostridium Difficile and Serum Levels of Igg Antibody Against Toxin A. The New England Journal of Medicine. Feb. 10, 2000, vol. 342, pp. 390-397.
Lagha et al., "Tea polyphenols inhibit the activation of NF-kB and the secretion of cytokines and matrix metalloproteinases by macrophages stimulated with Fusobacterium nucleatum", Nature, Oct. 2016, 6(34520):1-11.
Leng et al., "Transplantation of ACE2—Mesenchymal Stem Cells Improves the Outcome of Patients with COVID-19 Pneumonia", Aging and Disease, Mar. 2020, 11(2):216-228.
Li et al., "Dysbiosis of Gut Fungal Microbiota is Associated with Mucosal Inflammation in Crohn's Disease", J. of Clinical Gasteroenterology, Jul. 2014, 48(6):513-523.
MacFabe, "Short-chain fatty acid fermentation products of the gut microbiome: implications in autism prectrum disorder", Clinical Microbial Ecology in Health & Disease, Aug. 2012, 23(19260):1-25.
Mulle et al., "The Gut Microbiome: A New Frontier in Autism Research", Current Psychiatry Reports, Jan. 2013, 15(337):1-9.
Nigro et al., "A Placebo-Controlled Treatment Trial of Blastocystis hominis Infaction with Metronidazole", J. of Travel Medicine, 2003, 10:128-130.
Paquegnat et al., "A Vaccine and diagnostic target for Clostridium bolteae, an autism-assocciated bacterium", Vaccine, Apr. 2013, 31:2787.
PCT International Search Report and Written Opinion in International Application No. PCT/US2021/027139, dated Aug. 31, 2021, 16 pages.
Sullivan, "Candida dublinlensis: an emerging opportunistic pathogen", Current Topics in Medical Mycology, 1997, 8(1-2):15, 1 pages.
Vrieze et al., Fecal transplant: A safe and sustainable clinical therapyBasic Practice&Research in Clinical Gastronterology, 2013, 27:127.
Wang et al., "Increased abundance of Sutterella ssp. and Ruminococcus torques in feces of children with autism spectrum disorder", Molecular Autism, 2013, 4(42):1-4.
Yin et al., "Dysbiosis of Gut Microbiota with Reduced Trimethylamine-N-Oxide Level in Patients with Large-Artery Atherosclerotic Stroke of Transient Ischemic Attack", J. Ann. Heart Assoc., 2015, 4(11):1-23.
Zhang et al., "Changes in Intestinal Microbiota of Type 2 Diabetes in Mice in Response to Dietary Supplementation with Instant Tea or Matcha", Canadian Journal of Diabetes, May 2019, 44(1):44-52.
Bakken et al., "Treating Clostridium difficile Infection with Fecal Microbiota Transplantation", Clin. Gasteroenterol Hepatol, Dec. 2011, 9(12) :1044-1049.
Caporaso et al., "Global patterns of 16S rRNA diversity at a depth of millions of sequences per sample", PNAS, Mar. 2011, 108(Suppl. 1):4516-4522.
Faith et al., "The Long-Term Stability of the Human Gut Microbiota", Science, Jul. 2013, 340(44):1-10.
Goodman et al.,"Extensive personal human gut microbiota culture collections characterized and manipulated in gnotobiotic mice", PNAS, Apr. 2011, 108(15):6252-6257.
Hoveyda et al., "A systematic review and meta-analysis: probiotics in the treatment of irritable bowel syndrome", BMC Gastroenterology, Feb. 2009, 9(15):1-11.
Islam, "Clinical use of Probiotics", Medicine, Feb. 2016, 95(5):1-5.
Kelly, "Fecal Microbiota Transplantation—An old therapy comes of age", NEJM, Jan. 2013, 368(5):474-475.
Pham et al., "Emerging insights on intestinal dysbiosis during bacterial infections", Current Opinion in Microbiology, 2014, 17:67-74.
Wu et al., "WebMAG: A customizable web server for fast metagenomic sequence analysis", BMC Genomics, 2011, 12(444):1-9.
Van De Sande et al., "Autism and nutrition: the role of the gut-brain axis", Nutrition Research Reviews, Cambridge University Press, Dec. 2014, 27(2): 199-214.
Wang et al., "Low Relative Abundances of the Mucolytic Bacterium Akkermansia muciniphila and Bifidobacterium spp. in Feces of Children with Autism", Applied and Environmental Microbiology, Jul. 2011, 77(18): 6718-6721.
Van Hemert et al., "Clinical Studies Evaluating Effects of Probiotics on Parameters of Intestinal Barrier Function", Advances in Microbiology, Jan. 1, 2013, 3(2): 212-221.
Vyas et al., "Probiotics, Prebiotics, and Synbiotics: Gut and Beyond", Gastroenterology Research and Practice, vol. 2012, Jan. 1, 2012 (Jan. 1, 2012), pp. 1-16.
EP Partial European Search Report in European Application No. 19876127.2, dated Jun. 29, 2022, 24 pages.
JP Office Action in Japanese Application No. 2019-515430, dated Apr. 27, 2022, 13 pages (with English translation).
Chao and Shen, "Nonparametric Estimation of Shannon's index of diversity when there are unseen species in sample", Environmental and Ecological Statistics 10: 429-443 (2003).
CN Office Action in Chinese Application No. 201980082559.4, dated Jun. 20, 2022, 11 pages (with English translation).
CRIEPI News, 2007, No. 441, pp. 1-4 (with partial English translation).

(56) References Cited

OTHER PUBLICATIONS

JP Office Action in Japanese Application No. 2020-553639, dated Feb. 20, 2023, 8 pages (with English translation).

\* cited by examiner

FIG. 9

| DNA sequencing representation from extracted samples | | | |
|---|---|---|---|
| Unique ID with medium to high frequency | | Unique ID with low frequency | |
| Organism | Frequency | Organism2 | |
| Bacillus clausii | 445646 | Enterobacteria phage HK022 | |
| Bifidobacterium animalis 21389 Branch | 15681 | Lactobacillus phage A2 | |
| Pediococcus acidilactici MA18 5M | 7384 | Escherichia phage HK639 | |
| Acinetobacter indicus 41843 Branch | 5497 | Phage cdtI | |
| Lactobacillus salivarus DSM 20555 ATCC 11741 | 4693 | Saccharomyces kudriavzevii FM1094 | |
| Acinetobacter sp CIP 53 82 | 4385 | Saccharomyces pastorianus | |
| Bacillus amyloliquefaciens strain X1 | 3589 | Pseudomonas stutzeri 39512 Branch | |
| Bacillus phage phi 29 | 1633 | Lactobacillus acidophilus 5465 Branch | |
| Lactobacillus helveticus R0052 | 1565 | Saccharomyces cerevisiae EC98 | |
| Bacillus sp JS | 1259 | Kelbseilla 34709 Branch | |
| Saccharomyces sp. Boulardii | 992 | Sclerotinia sclerotiorum partitivirus S segment 2 | |
| Bacillus subtilis strain D7XPN1 | 832 | Burkholderia phage BcepMu | |
| Lactobacillus plantarum 5223 Branch | 736 | Enterobacter cloacae strain 36500 Branch | |
| Bifidobacterium longum subsp infantis EK3 | 614 | Lactococcus prophage blL311 | |
| Enterococcus hirae | 513 | Enterococcus phage phiFL4A | |
| Lactobacillus debrueckii subsp bulgaricus ATCC BAA 365 | 328 | Streptococcus phage SM1 | |
| Enterococcus 5215 Branch | 316 | Bacillus coagulans | |
| Lactobacillus rhamnosus 5677 Branch | 239 | | |
| Lactococcus lactis s 4140 Branch | 236 | | |

FIG. 10

| UNIQUE SPECIES IN DATABASE | |
|---|---|
| ARCHAEA | 676 |
| BACTERIA | 94,641 |
| FUNGI | 238 |
| PROTOZOA | 79 |
| VIRUSES | 7,497 |
| TOTAL | 103,131 |

Rough physical assessment:
Ethnicity: Asian
DOB: Jan 22, 19XX
BMI:24.7
Fitness:
Energy level 4/5

Survey results
-
nutrition
Protein shakes/supplements:
No

Caffeine:
Yes

Alcohol:
1 glass of wine/ beer per week

Smokes:
No

Antibiotics:
No
Probiotic foods? (Yoghurt etc.):
Yes

Nutritional
supplements:
N/A

Food before collection:
Chicken, Pork & Beef
Rice vegetables seafood

FIG. 11

UNIVERSAL METHOD FOR EXTRACTING NUCLEIC ACID MOLECULES FROM A DIVERSE POPULATION OF ONE OR MORE TYPES OF MICROBES IN A SAMPLE

CROSS REFERENCE TO RELATED APPLICATIONS

This application is a continuation-in-part application of U.S. application Ser. No. 16/042,831 filed on Jul. 23, 2018, which is a divisional application of U.S. application Ser. No. 15/824,754 filed Nov. 28, 2017, which is a continuation application of International Application No. PCT/US2017/051849 filed Sep. 15, 2017, which claims the benefit under 35 U.S.C. § 119(e) to U.S. Application Ser. No. 62/412,787 filed Oct. 25, 2016 and to U.S. Application Ser. No. 62/395,316 filed Sep. 15, 2016; and this application claims the benefit under 35 U.S.C. § 119(e) to U.S. Application Ser. No. 62/651,620 filed Apr. 2, 2018. The disclosure of each of the prior applications is considered part of and is incorporated by reference in the disclosure of this application.

BACKGROUND OF THE INVENTION

Field of Invention

The present invention relates generally to genomic analysis and more particularly to a method of extracting and analyzing nucleic acid molecules associated with food from a diverse population of microbes in a biological sample.

Background Information

About 100 trillion microorganisms live in and on the human body vastly outnumbering the body's approximately 10 trillion human cells. These normally harmless viruses, bacteria and fungi are referred to as commensal or mutualistic organisms. Commensal and mutualistic organisms help keep our bodies healthy in many ways. Together all of the microorganisms living in and on the body—commensal, mutualistic and pathogenic—are referred to as the microbiome and their equilibrium and associated metabolome is closely linked to an individual's health status and vice-versa.

Advances in nucleic acid sequencing has created an opportunity to quickly and accurately identify and profile the microbiome inhabiting the gut and subcutaneous tissue. The optimal flora also interacts with the host immune system in a synergistic way further propagating its health benefits. The associated metabolome of individuals can also be profiled either by a mass-spectrometry based system or using genomics-based metabolome modeling and flux-balance analysis and used to make a healthy metabolome profile. All these methodologies can be used to dissect the complexity of microbial communities.

SUMMARY OF THE INVENTION

The present invention is directed to a method of extracting nucleic acid molecules from a diverse population of microbes in a biological, environmental, dietary supplement, or other ecological microbial organism heterogeneous populations sample and use of nucleic acid or extracts through processing steps and analysis for the determination of probiotic customization to an individual. Processing steps specific to this invention include, RNA or DNA clean-up, fragmentation, separation, or digestion; library or nucleic acid preparation for downstream applications, such as PCR, qPCR, digital PCR, or sequencing; preprocessing for bioinformatic QC, filtering, alignment, or data segregation; metagenomics or human genomic bioinformatics pipeline for microbial species taxonomic assignment; and other organism alignment, identification, and variant interpretation.

The present invention also describes a universal method for using samples for DNA extraction and determination of food consumption based on food DNA sequence from a database of meats, plants, fruits, vegetables, and/or microbes contained with these organisms. Disclosed herein are methods of extracting genetic material from a diverse population of one or more types of cells or cell components in a sample and determining the consumed food and nutritional breakdown for the improvement of health and prevention of disease.

Accordingly, in one aspect, the invention provides a method for preparing a sample for analysis. The method includes: a) mixing the sample with a first lysis solution comprising a detergent, e.g., SDS, and a chelator, e.g., EDTA; b) adding a second lysis solution having a lysozyme to the mixture of step a); and c) adding a third lysis solution comprising a chaotropic agent, e.g., urea, lithium acetate, guanidine hydrochloride, and the like, to the mixture of step b). Pre-processing steps may include physical lysis may be used to further optimize nucleic acid yield. Examples of mechanical lysis include sonication, bead mixing, and bead mill homogenization.

In a similar aspect, the method includes: a) mixing a sample, such as a stool sample, with a liquid nitrogen solution; b) adding a first lysis solution, the first lysis solution comprising a detergent and a chelator, e.g., SDS, and a chelator, e.g., EDTA; and c) adding a second lysis solution, the second lysis solution including a chaotropic agent, e.g., urea, lithium acetate, guanidine hydrochloride. Pre-processing steps may include physical lysis may be used to further optimize nucleic acid yield. Examples of mechanical lysis include sonication, bead mixing, and bead mill homogenization.

In another aspect, the invention provides a method of determining food consumption of a subject. The method includes: a) extracting genetic material from a stool sample obtained from the subject, said genetic material extracted according to a method of the disclosure; and b) subjecting the genetic material extracted from the first sample to metagenomics analysis to determine the food consumption of the subject. In embodiments, the method further includes treating the subject with a probiotic or a food stuff based on the analysis of food consumption.

In another aspect, the invention provides a method of monitoring a probiotic treatment of a subject. The method includes: a) extracting genetic material from any microbes present in a first sample obtained from the subject, said genetic material extracted according to a method of the disclosure; b) subjecting the genetic material extracted from the first sample to metagenomics analysis; c) treating the subject with a probiotic and then extracting genetic material from any microbes present in a second sample obtained from the subject in the same manner as the extraction of genetic material from the first sample; d) performing metagenomics analysis on the extracted genetic material from the second sample; and e) comparing the results of the metagenomics analysis of the first sample with the metagenomics analysis of the second sample.

In yet another aspect, the invention provides a method comprising calculating a probiotic score from probiotic organisms detected in a gut with or without additional chemistry or genetic tests.

In still another aspect, the invention provides a method comprising calculating a score for a microbiome, the score being used to assess if the microbiome is in dysbiosis, neutral, or stable.

The invention further provides a computing system comprising: a memory; and one or more processors coupled to the memory, the one or more processors configured to perform operations to perform a method of the present invention.

The invention also provides an automated platform for performing a method of the invention.

The invention provides an all-in-one method for extracting nucleic acids from a diverse flora of microbes from a biological, environmental, dietary supplement, or other ecological microbial organism heterogeneous populations sample.

In embodiments, the invention may be used in determining composition and relative abundance of microbes, via analyzing their respective nucleic acids, in probiotics and environmental samples. DNA is purified and used downstream for nucleic acid analysis (notably metagenomics analysis where genome of more than one species/subspecies is identified).

Both the foregoing general description and the following detailed description are exemplary and explanatory only and are intended to provide further explanation of the invention as claimed. Any accompanying drawings are included to provide a further understanding of the invention and are incorporated in and constitute part of this specification, illustrate several embodiments of the invention, and together with the description serve to explain the principles of the invention.

BRIEF DESCRIPTION OF THE DRAWINGS

FIG. 9 is a table setting forth organisms identified via the method of the invention from a dietary supplement mixed culture.

FIG. 10 is a table setting forth the classification of unique species of various microbes stored in the database of the invention.

FIG. 11 illustrates example demographic information from an individual in one embodiment of the invention.

DETAILED DESCRIPTION OF THE INVENTION

Figure 1:
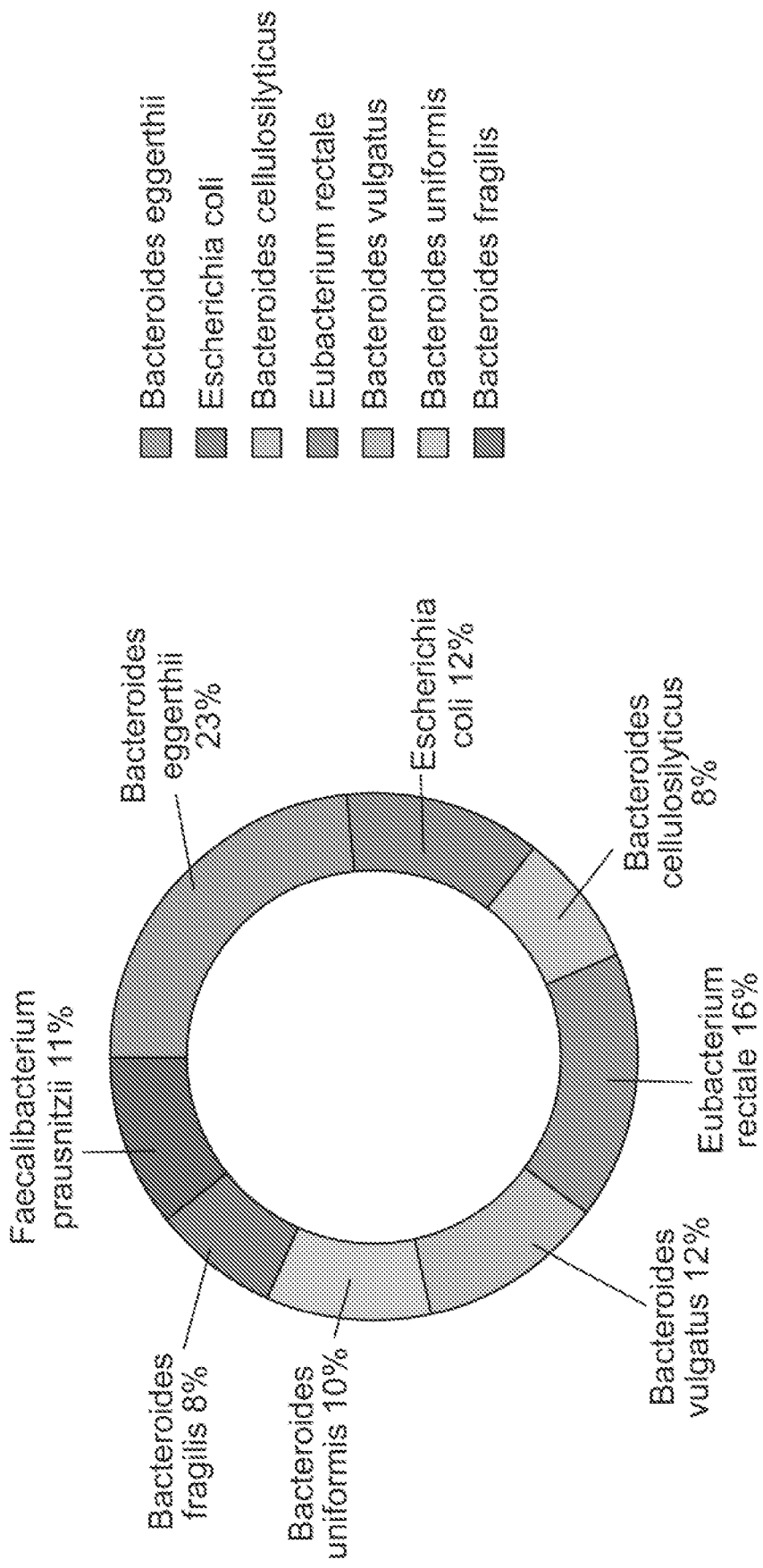
FIG. 1 is a schematic diagram illustrating the presence of high prevalence organisms of a microbiome signature of a human (high protein diet, >50 years old, supplement user).
Figure 2A:
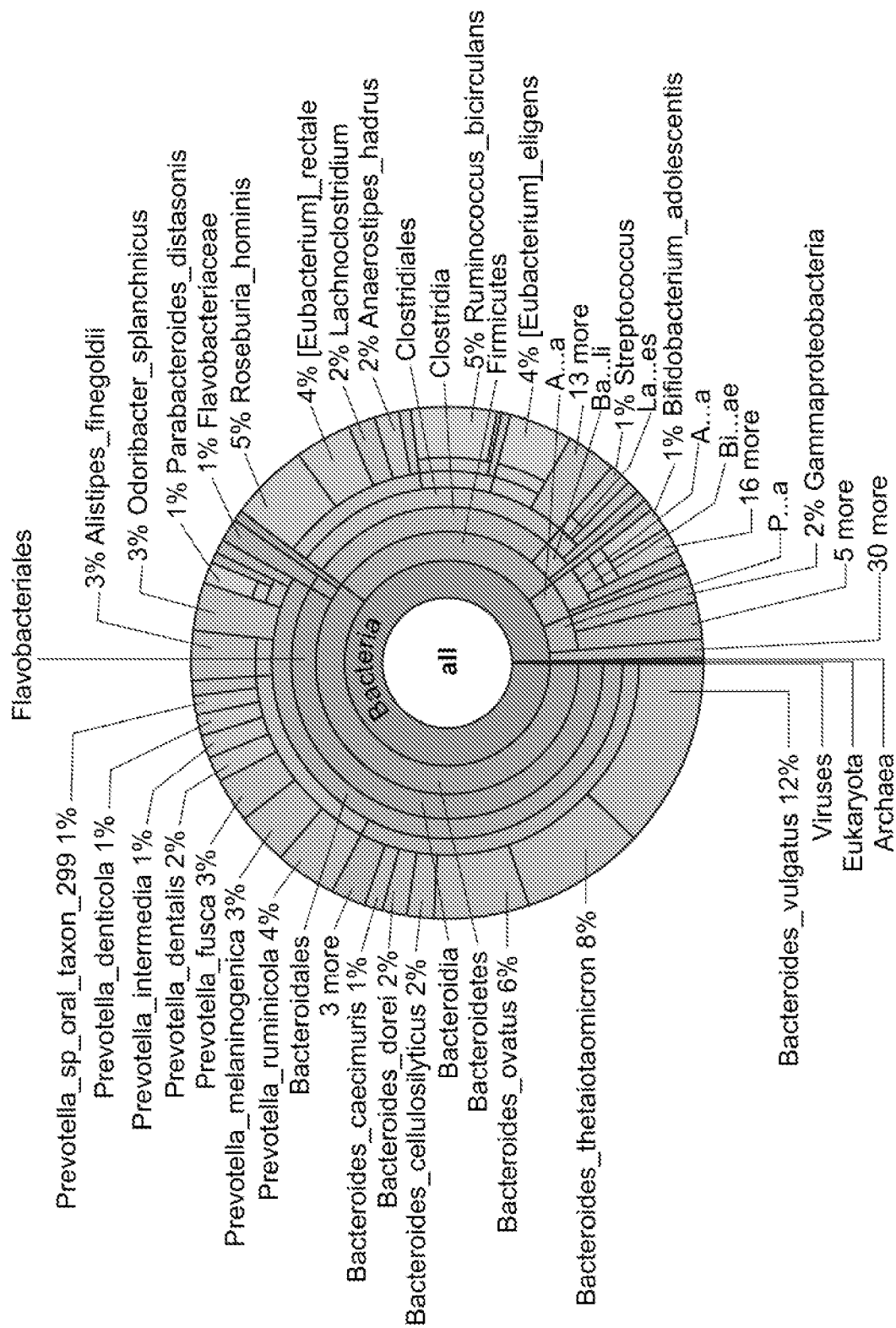
FIG. 2A is a schematic diagram illustrating the presence of high prevalence organisms (bacteria) of a microbiome signature of a human (high carbohydrate diet, 18-50 years old, vegetarian diet).
Figure 2B:
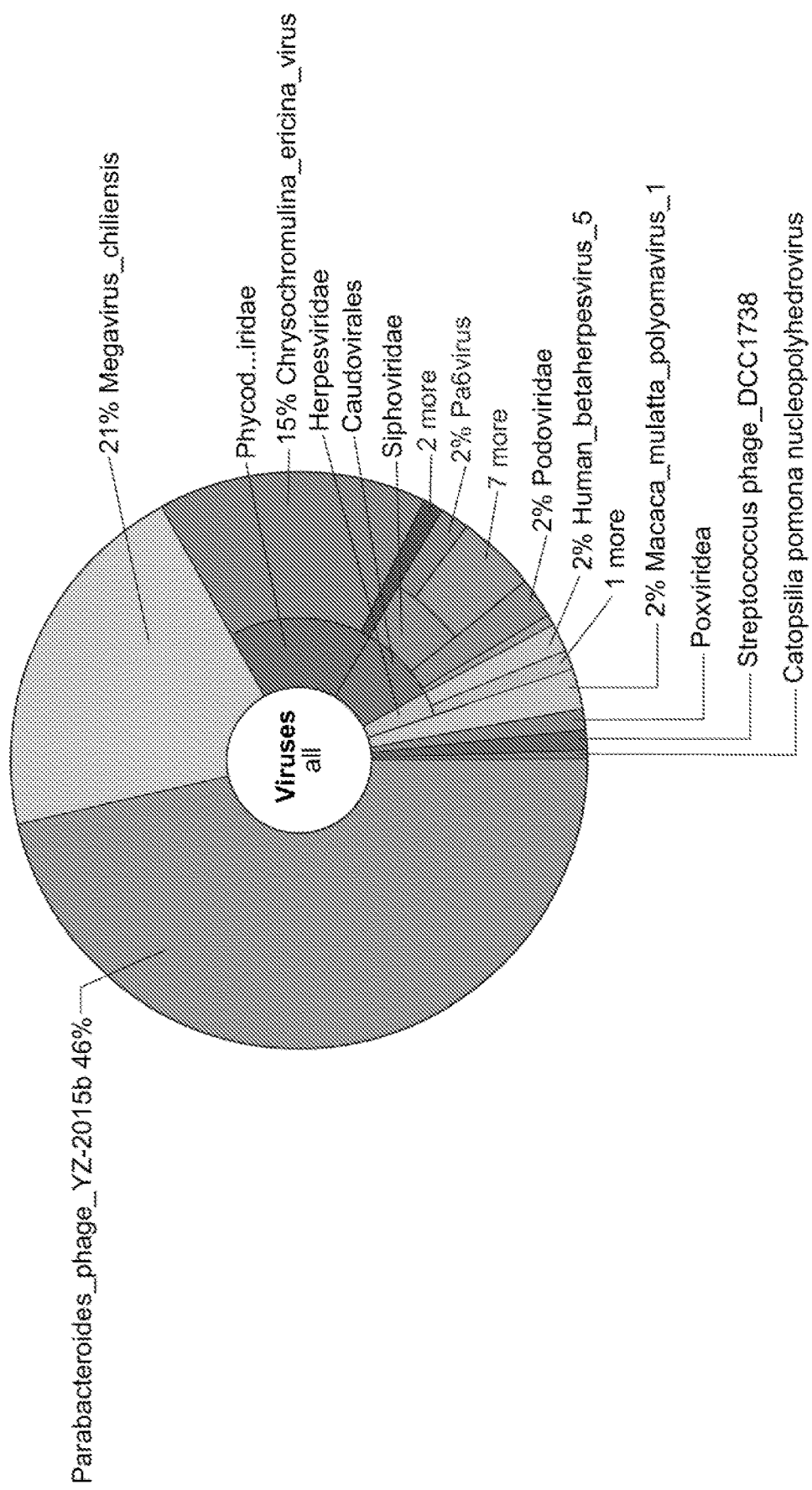
FIG. 2B is a schematic diagram illustrating the presence of high prevalence organisms (viruses and phages) of a microbiome signature of a human (high carbohydrate diet, 18-50 years old, vegetarian diet).
Figure 2C:
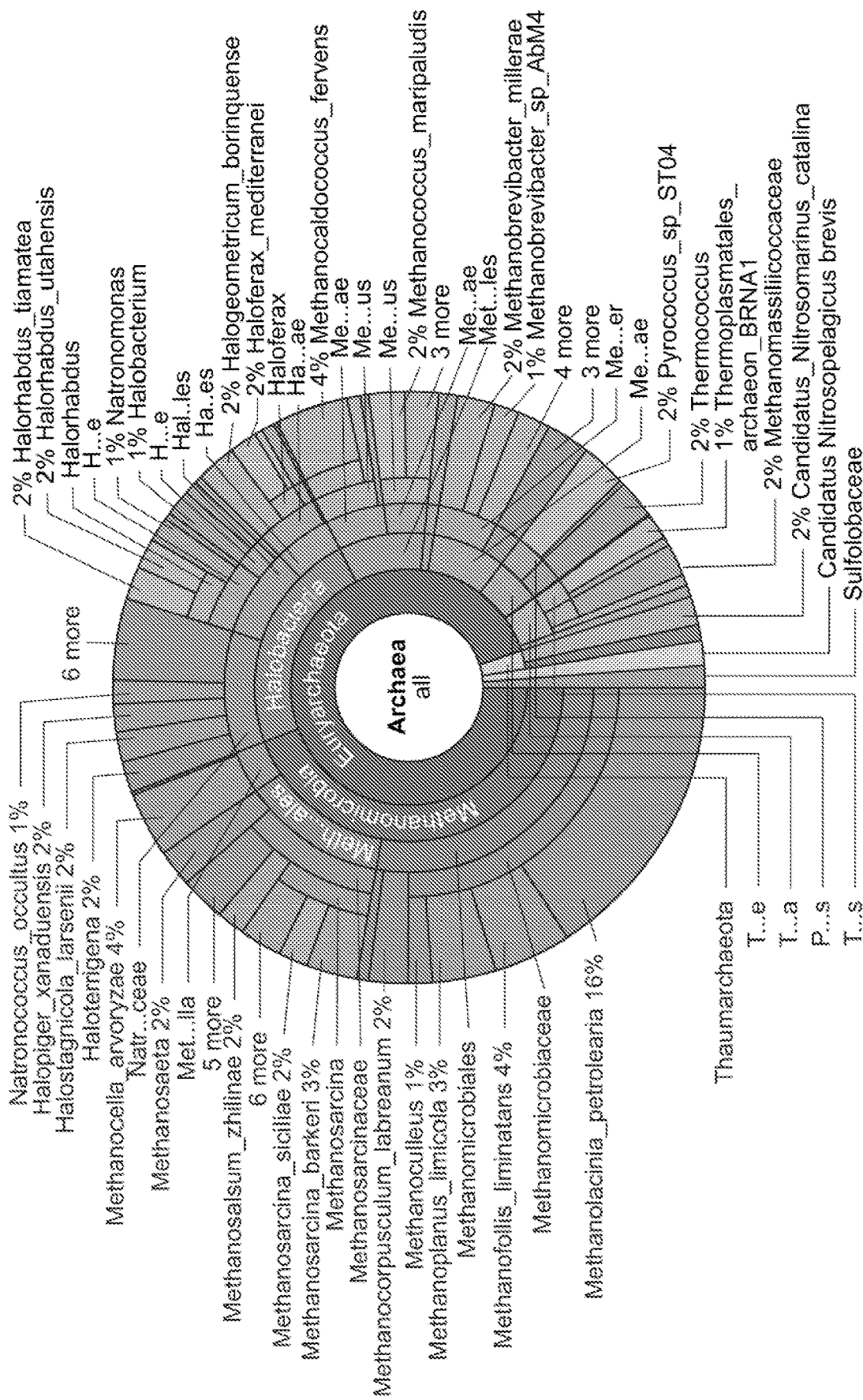
FIG. 2C is a schematic diagram illustrating the presence of high prevalence organisms (archaea) of a microbiome signature of a human (high carbohydrate diet, 18-50 years old, vegetarian diet).
Figure 2D:
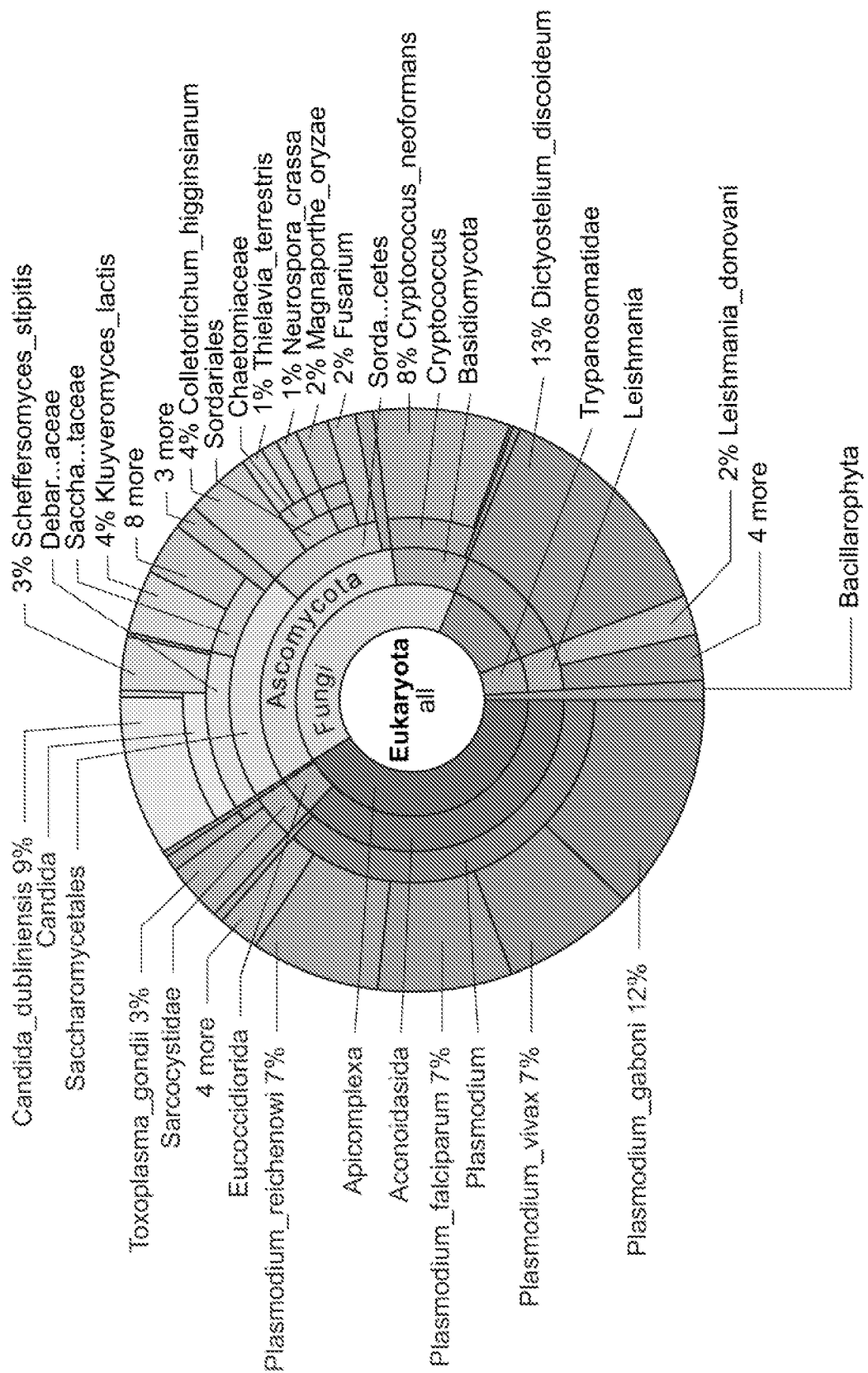
FIG. 2D is a schematic diagram illustrating the presence of high prevalence organisms (fungi and other eukaryotes) of a microbiome signature of a human (high carbohydrate diet, 18-50 years old, vegetarian diet).
Figure 3A:
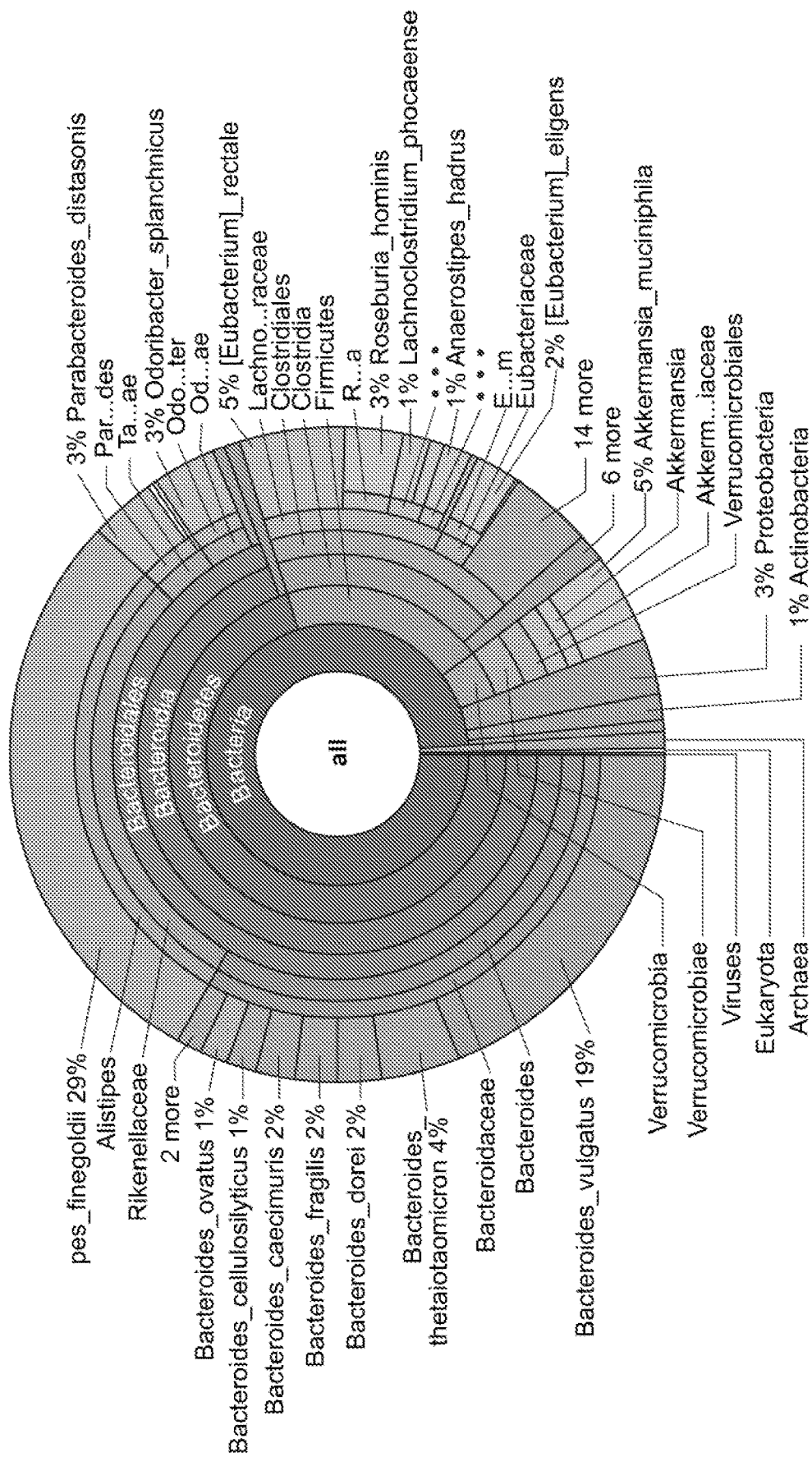
FIG. 3A is a schematic diagram illustrating the presence of high prevalence organisms (bacteria) of a microbiome signature of a human (high carbohydrate diet, 18-50 years old, non-vegetarian diet).
Figure 3B:
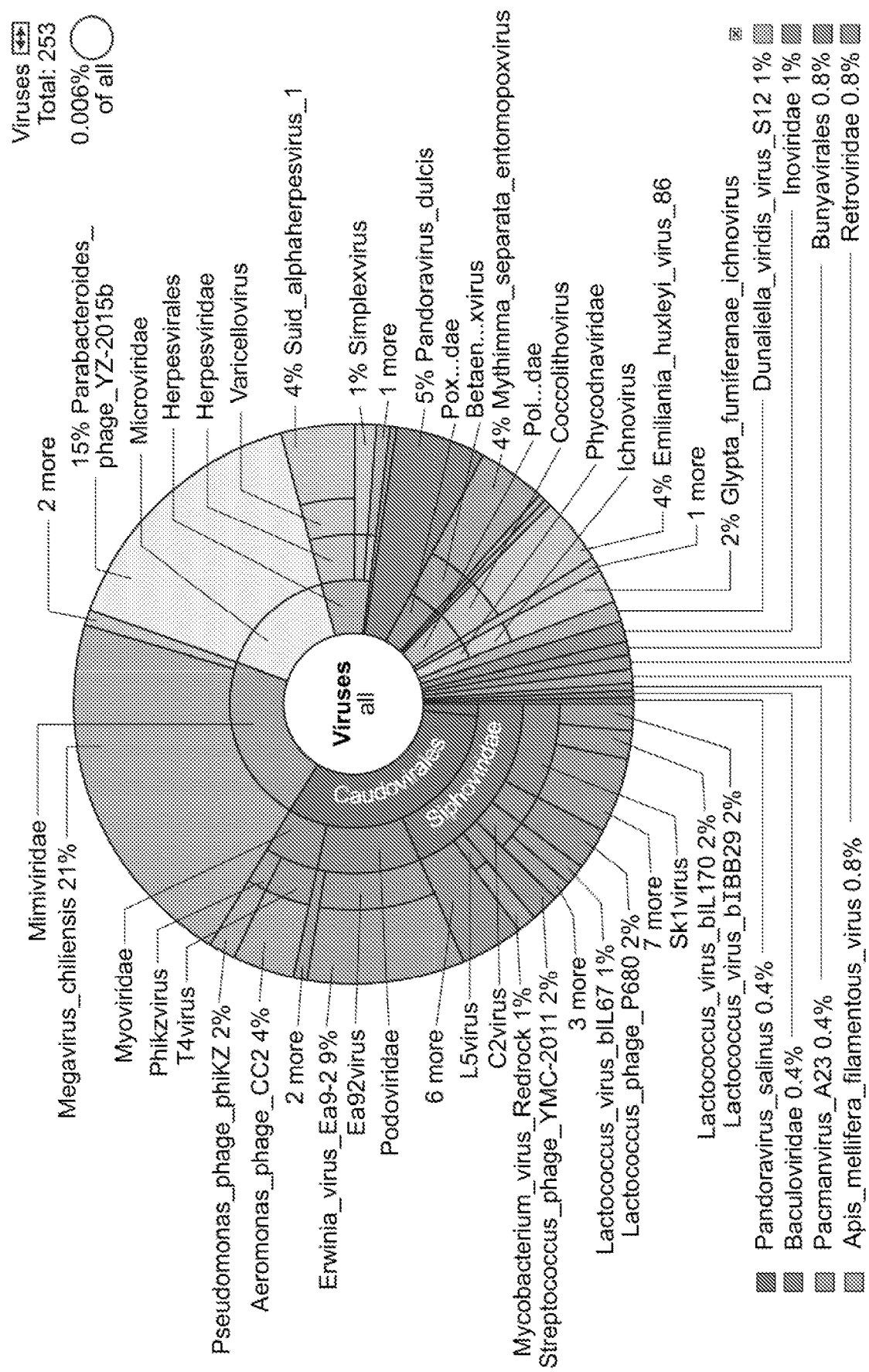
FIG. 3B is a schematic diagram illustrating the presence of high prevalence organisms (viruses and phages) of a microbiome signature of a human (high carbohydrate diet, 18-50 years old, non-vegetarian diet).
Figure 3C:
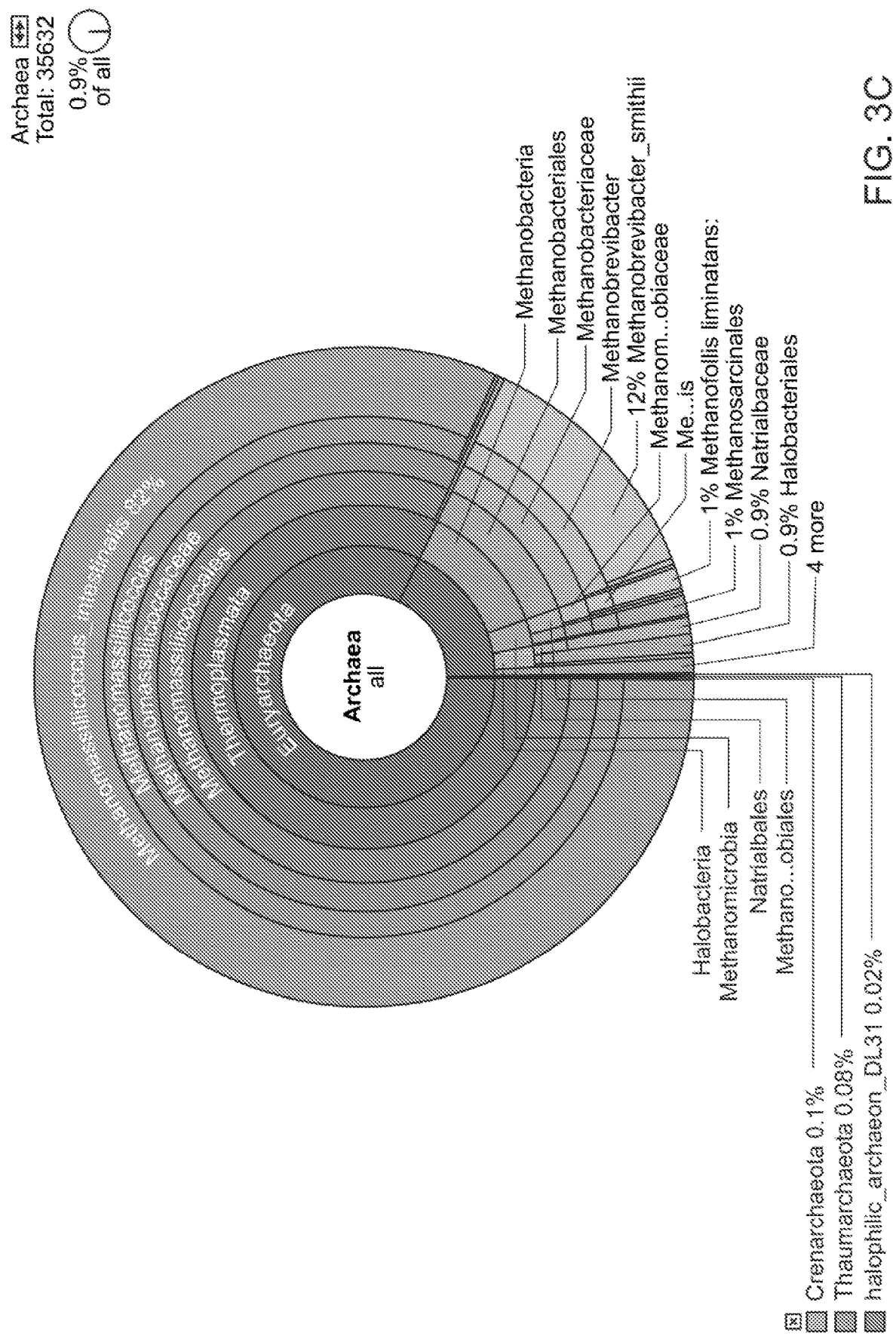
FIG. 3C is a schematic diagram illustrating the presence of high prevalence organisms (archaea) of a microbiome signature of a human (high carbohydrate diet, 18-50 years old, non-vegetarian diet).
Figure 3D:
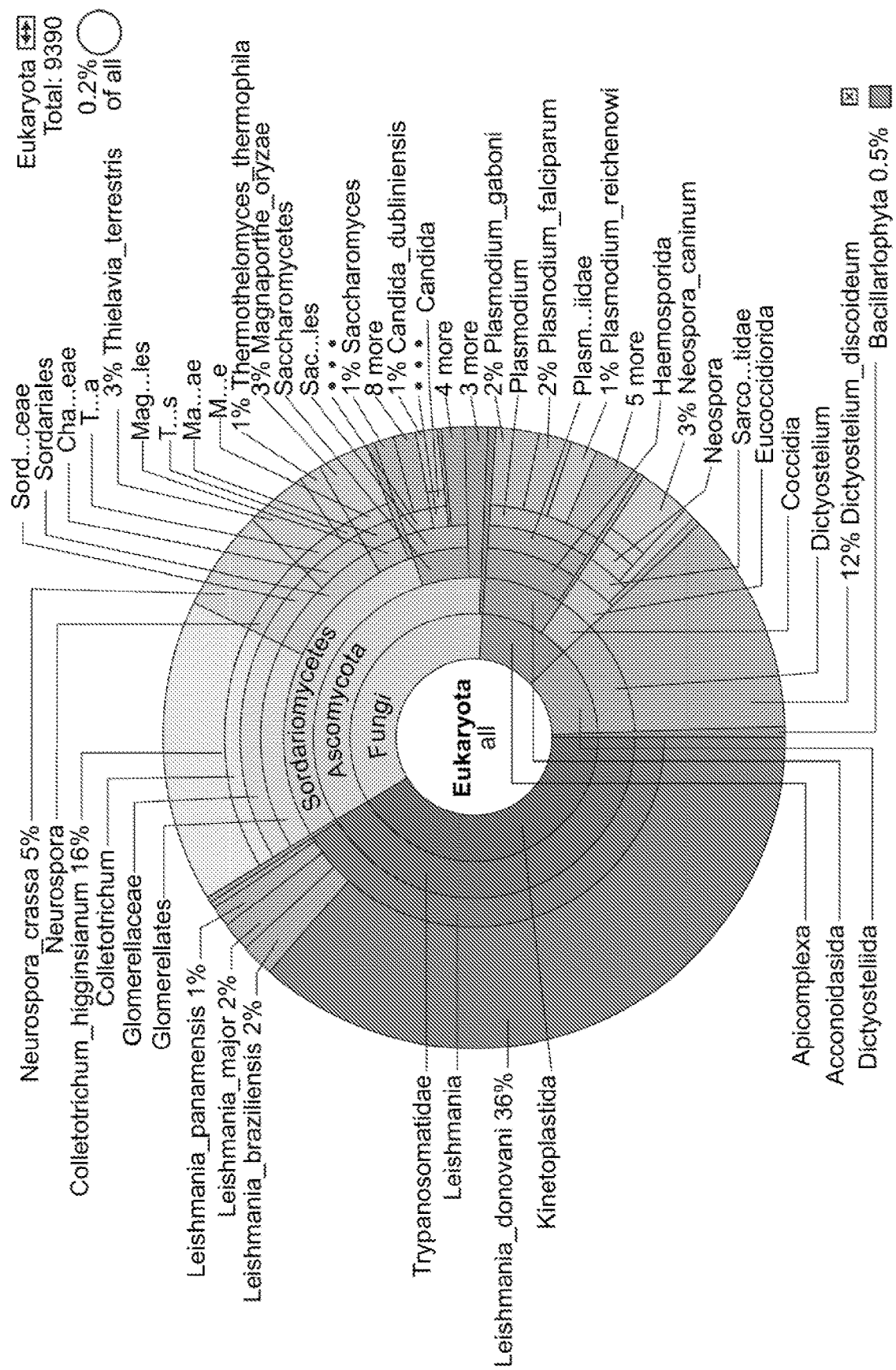
FIG. 3D is a schematic diagram illustrating the presence of high prevalence organisms (fungi and other eukaryotes) of a microbiome signature of a human (high carbohydrate diet, 18-50 years old, non-vegetarian diet).
Figure 4A:
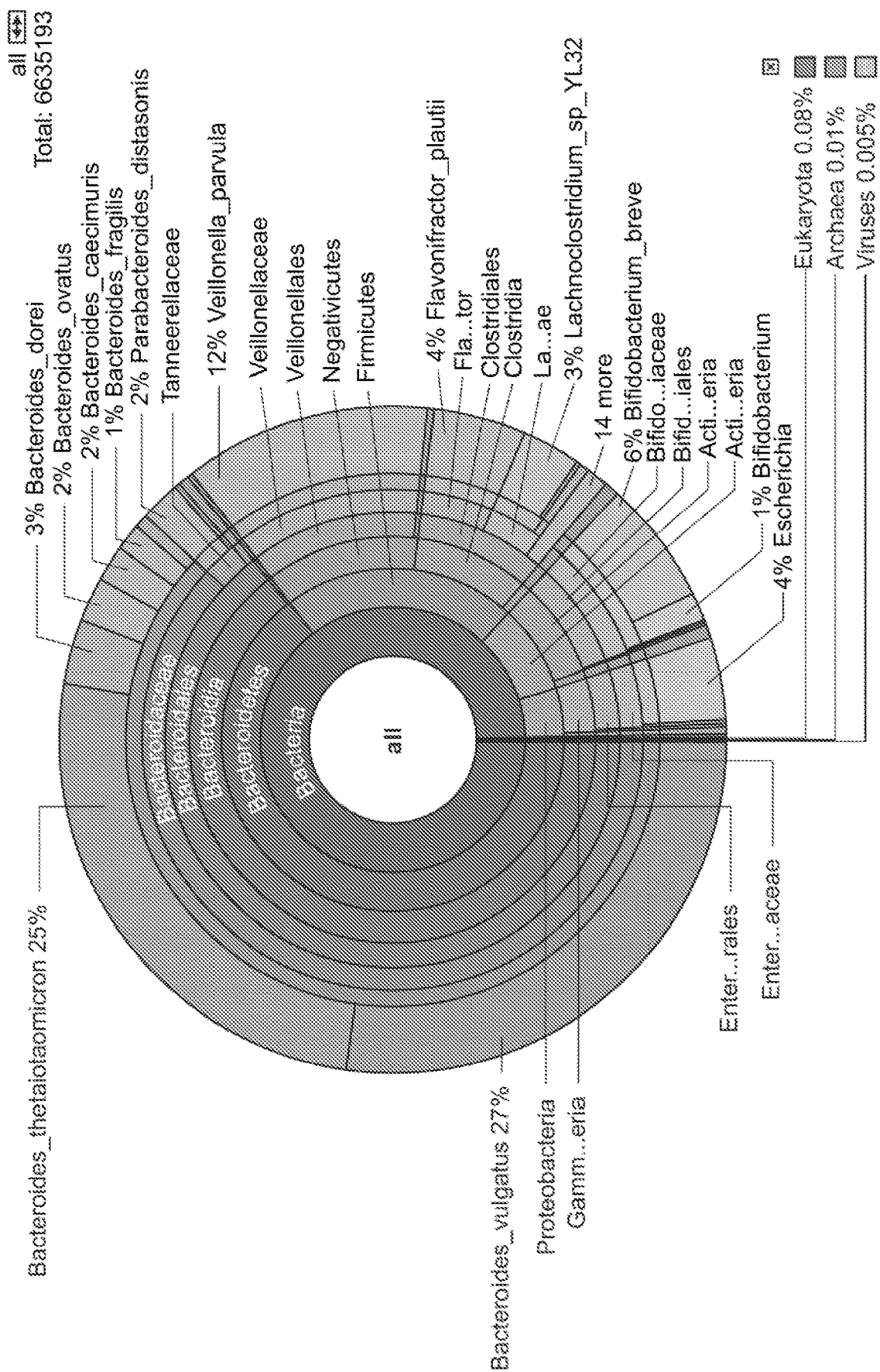
FIG. 4A is a schematic diagram illustrating the presence of high prevalence organisms (bacteria) of a microbiome signature of a human (high dairy protein diet, 0-2 years old, vegetarian non-nursing).
Figure 4B:
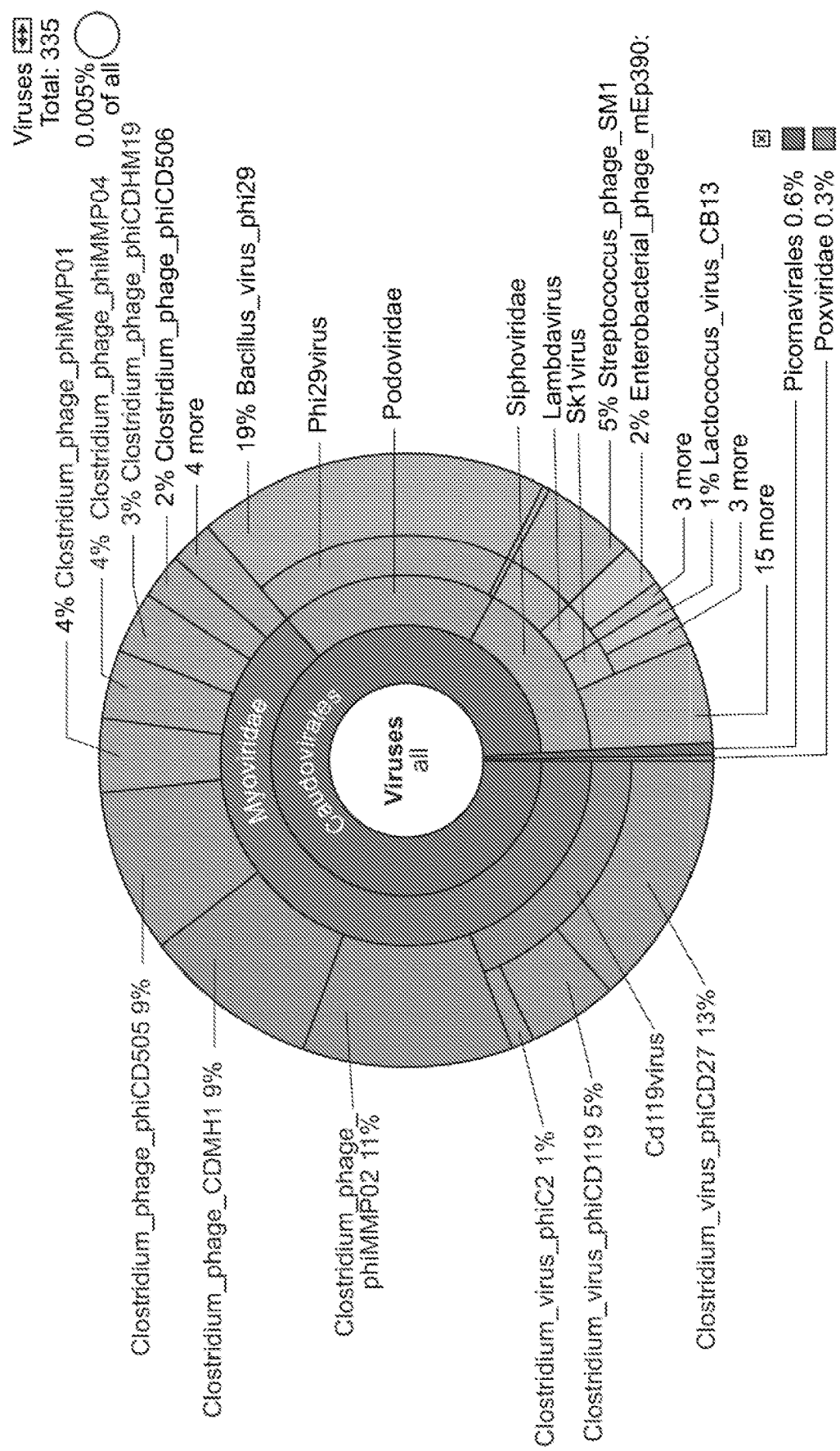
FIG. 4B is a schematic diagram illustrating the presence of high prevalence organisms (viruses and phages) of a microbiome signature of a human (high dairy protein diet, 0-2 years old, vegetarian non-nursing).
Figure 4C:
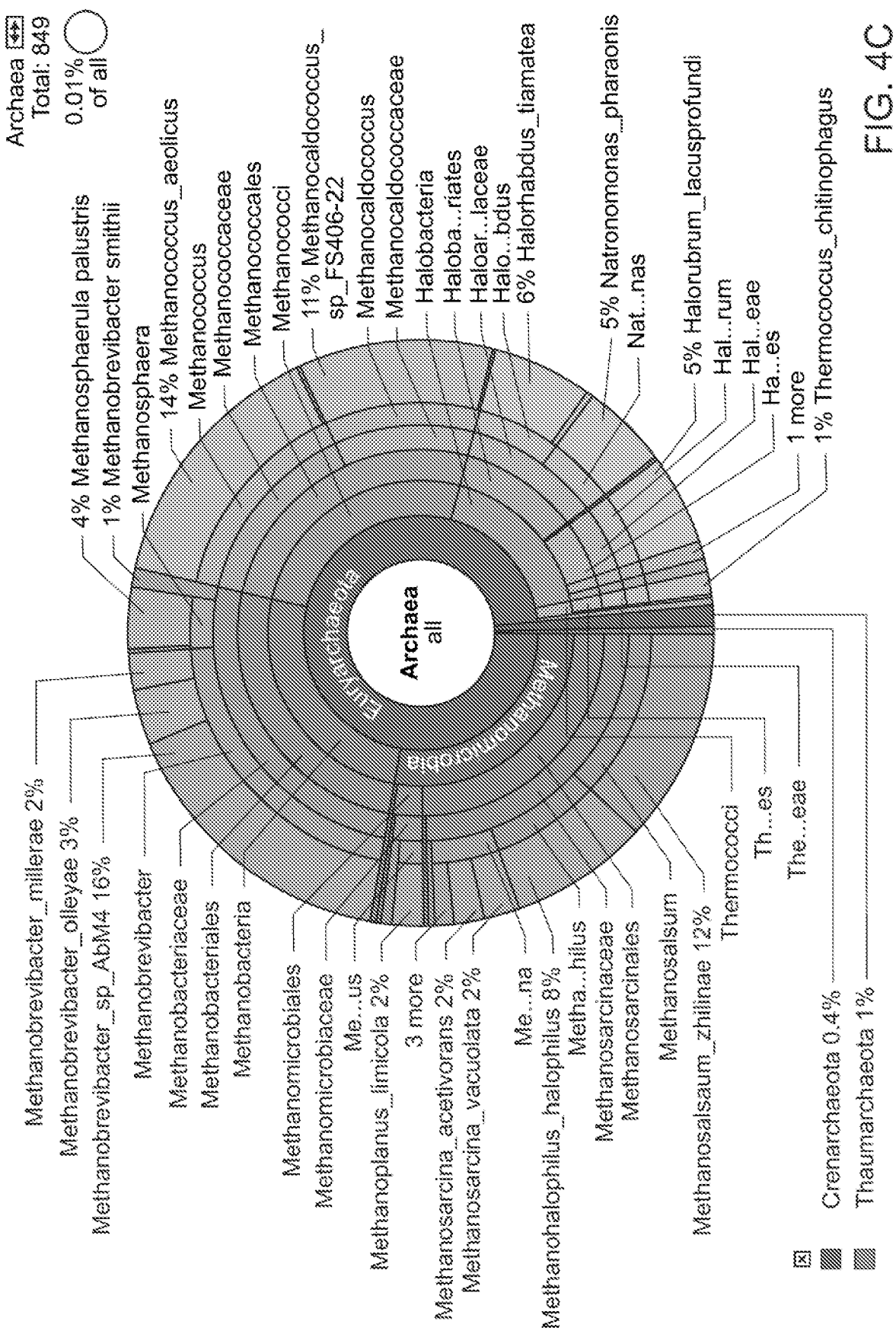
FIG. 4C is a schematic diagram illustrating the presence of high prevalence organisms (archaea) of a microbiome signature of a human (high dairy protein diet, 0-2 years old, vegetarian non-nursing).
Figure 4D:
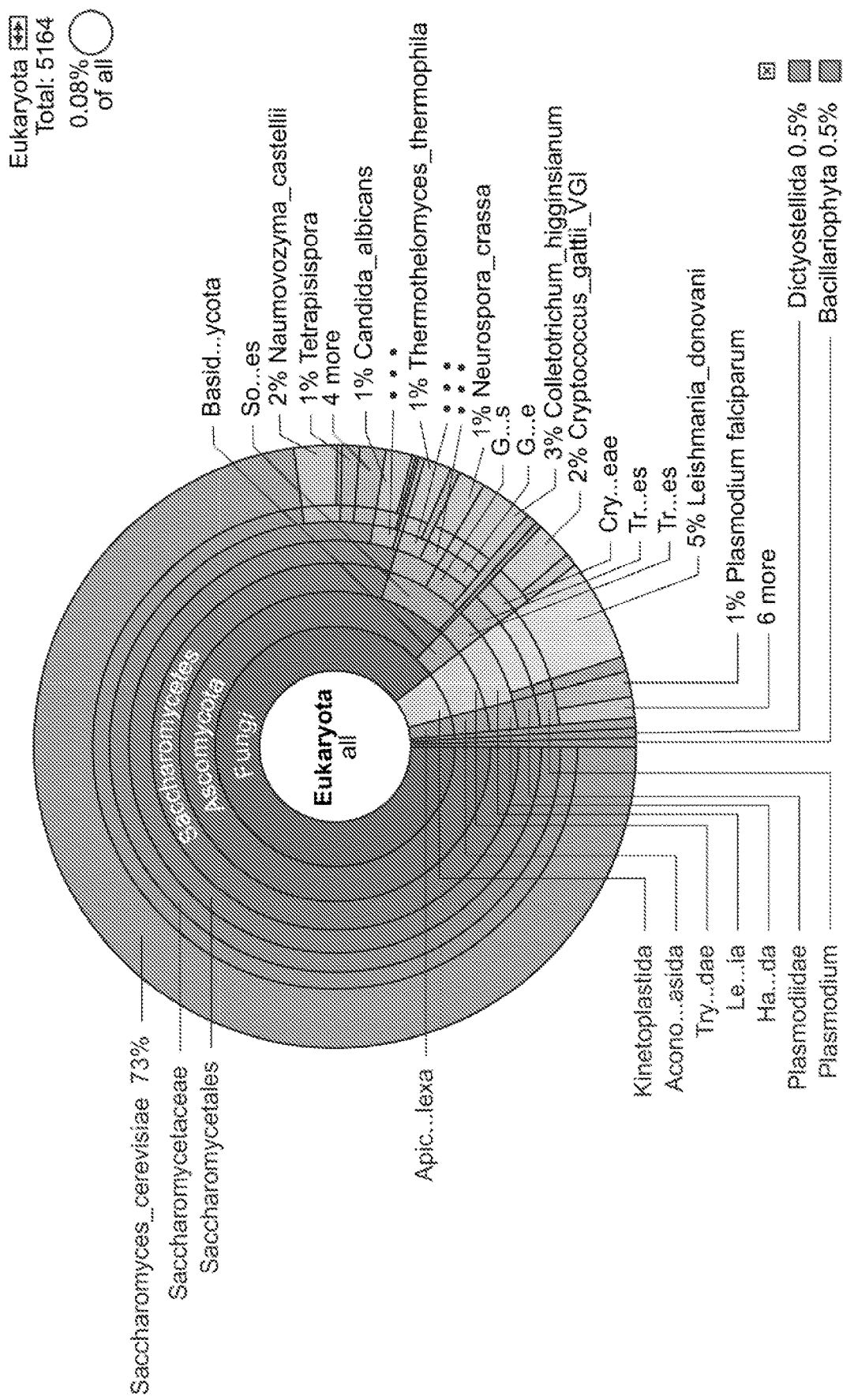
FIG. 4D is a schematic diagram illustrating the presence of high prevalence organisms (fungi and other eukaryotes) of a microbiome signature of a human (high dairy protein diet, 0-2 years old, vegetarian non-nursing).
Figure 5:
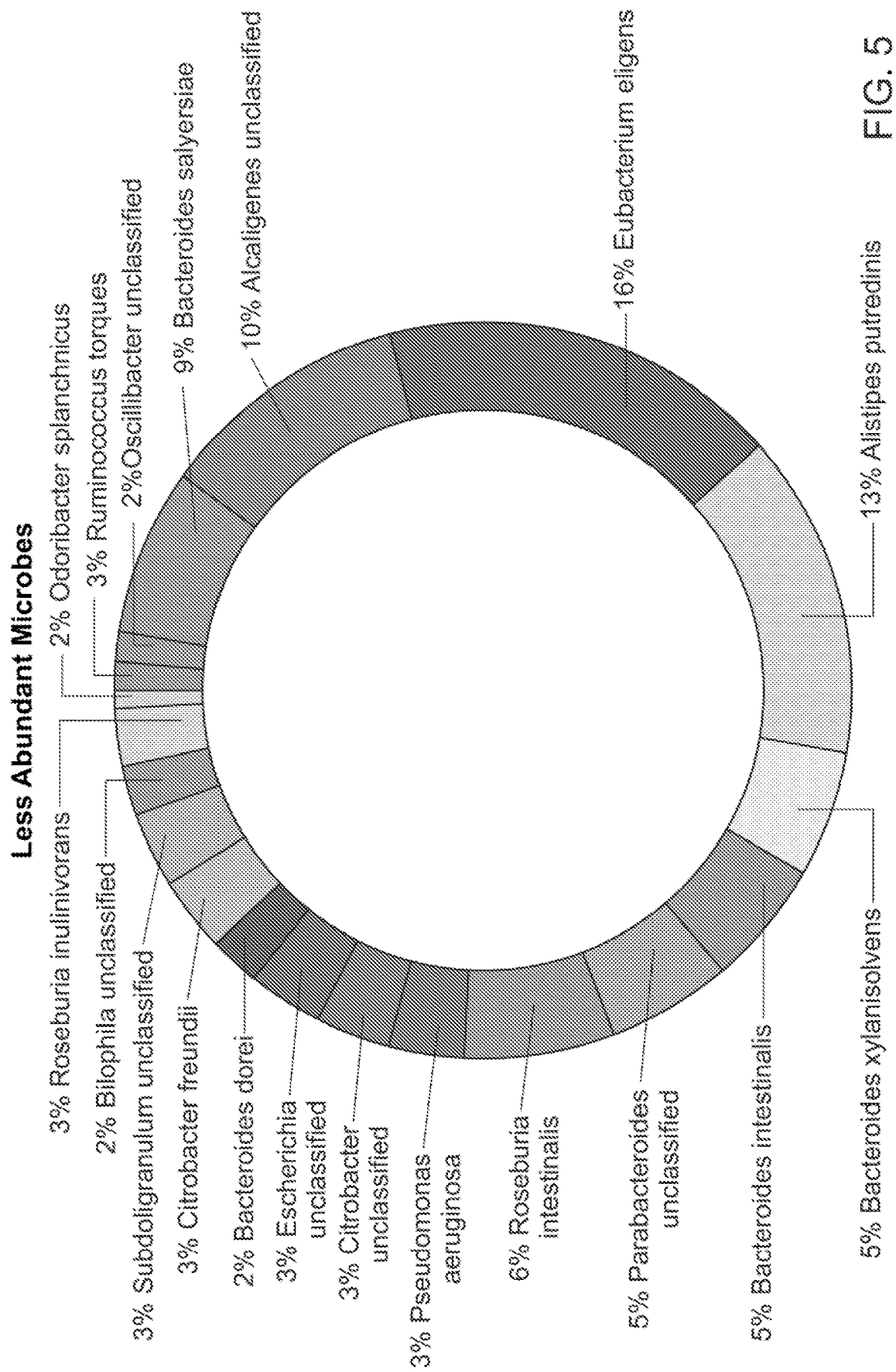
FIG. 5 is a schematic diagram illustrating the presence lower prevalent organisms and identification of opportunistic pathogens of a microbiome signature of a human.
Figure 6:
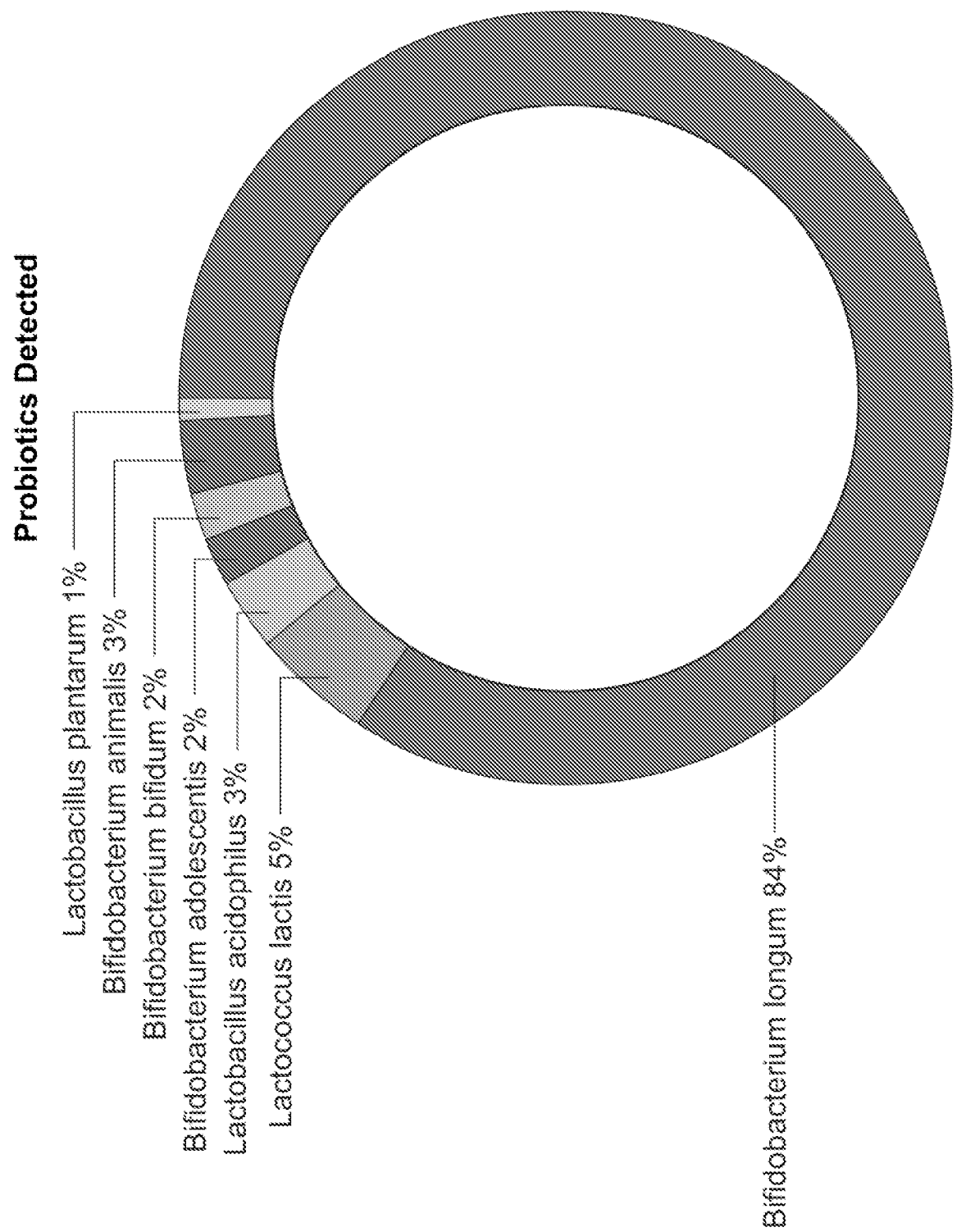
FIG. 6 is a schematic diagram illustrating typical probiotics detected in a microbiome signature of a human.
Figure 7:
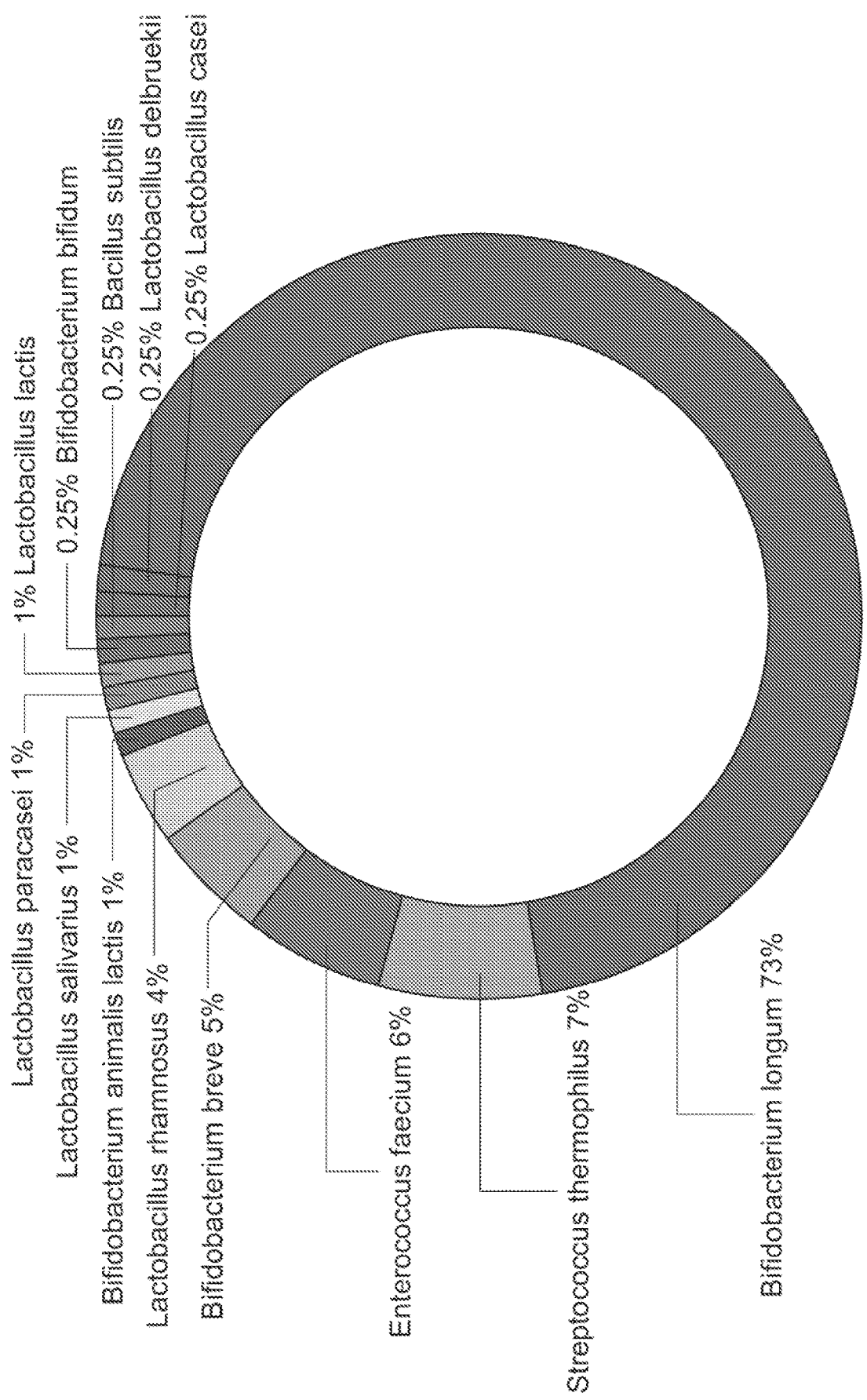
FIG. 7 is a schematic diagram illustrating typical probiotics detected in a microbiome signature of a human.
Figure 8:
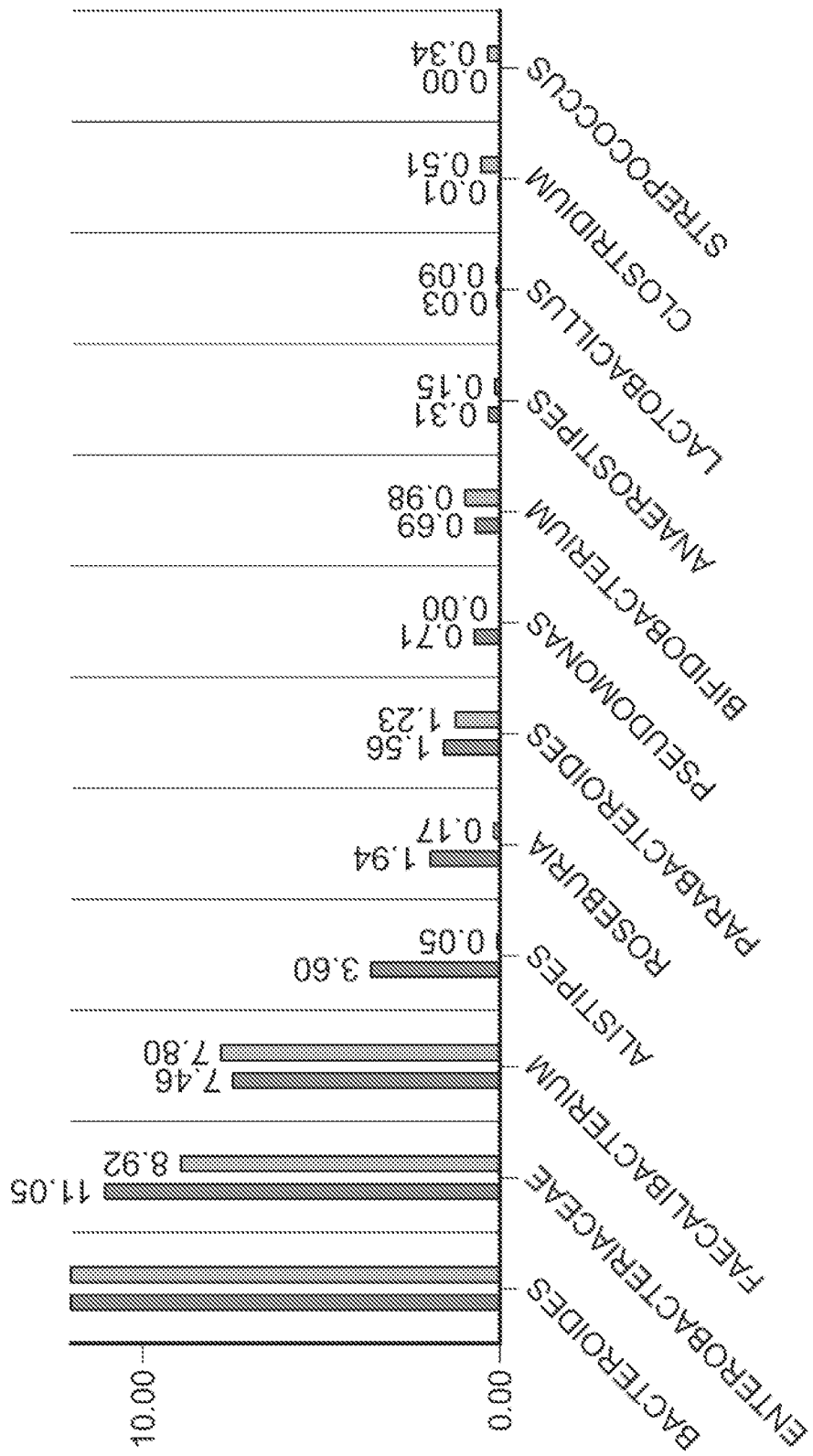
FIG. 8 is a schematic graphical plat illustrating showing comparison of individual relative abundance to database average for normal population.
Figure 12:
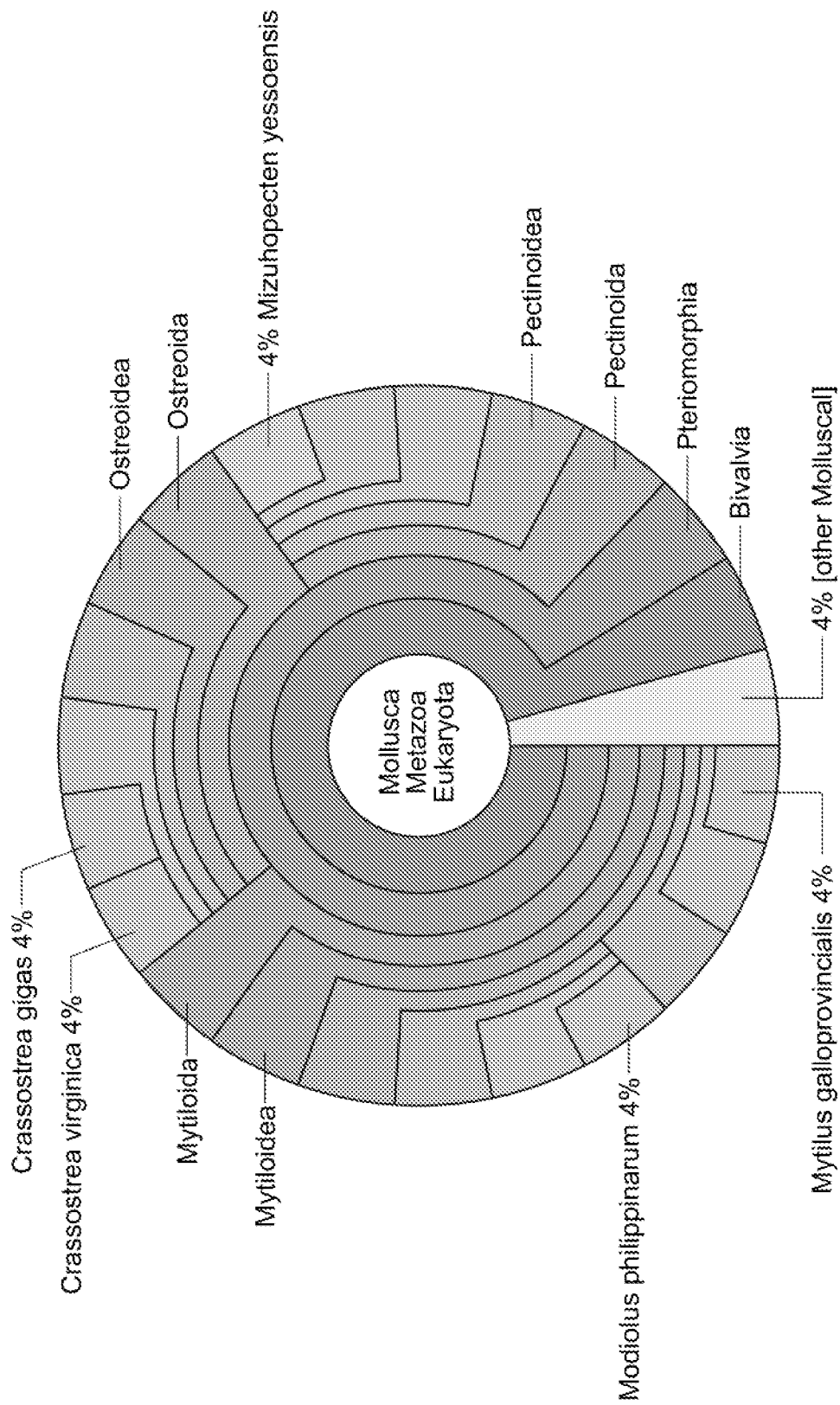
FIG. 12 illustrates example organisms detected related to seafood in one embodiment of the invention.
Figure 13:
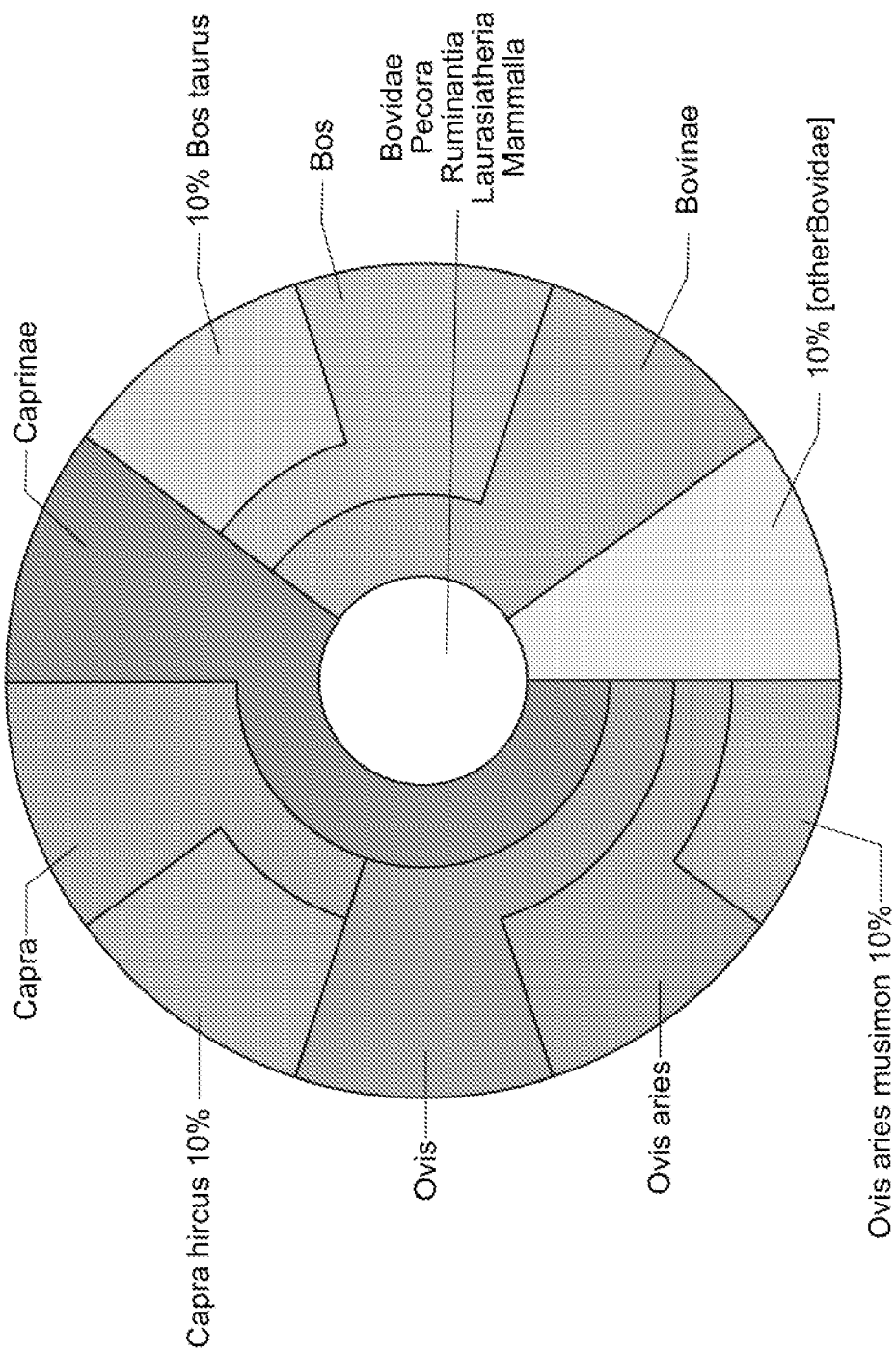
FIG. 13 illustrates example organisms detected related to mammalian meats in one embodiment of the invention.
Figure 14:
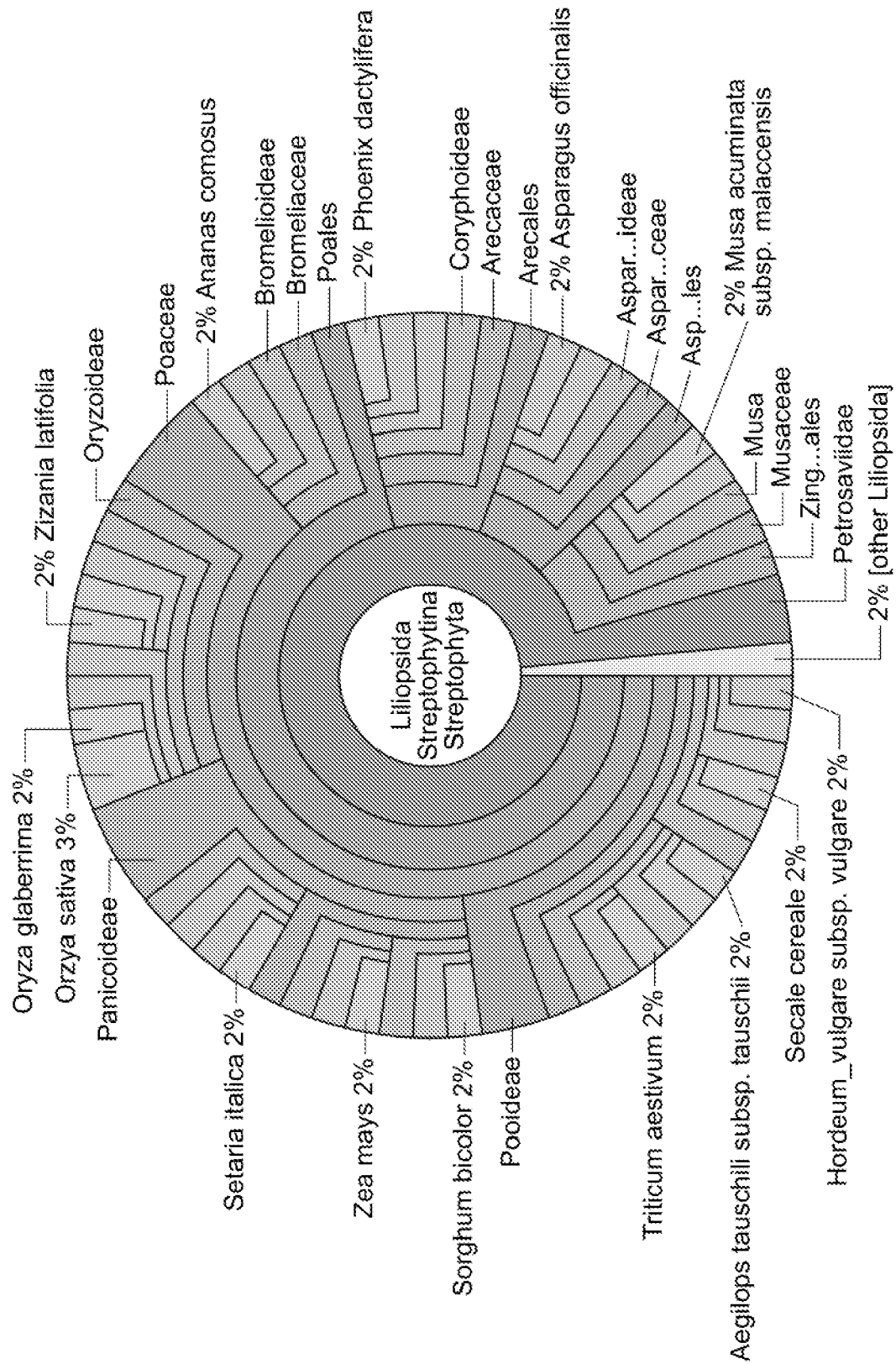
FIG. 14 illustrates example organisms detected related to grains in one embodiment of the invention.

The present invention provides a universal method for extracting nucleic acid molecules from a diverse population of one or more types of microbes in a sample. The types of microbes include: gram-positive bacteria, gram-positive bacterial spores, gram-negative bacteria, archaea, protozoa, helminths, algae, fungi, fungal spores, viruses, viroids, bacteriophages, and rotifers. In some embodiments, the diverse population is a plurality of different microbes of the same type, e.g., gram-positive bacteria. In some embodiments, the diverse population is a plurality of different types of microbes, e.g., bacteria (gram-positive bacteria, gram-positive bacterial spores and/or gram-negative), fungi, viruses, and bacteriophages.

Because different types of microbes have different compositions and mechanisms to protect their own genetic material it is often difficult to extract the genetic material from one type of microbe without compromising the ability to also extract the genetic material of another type of microbe in the same biological sample. The present invention, however, allows the extraction of genetic material from different types of microbes in a sample without sacrificing the amount of genetic material that can be obtained from one type of microbe by extracting the genetic material of another type of microbe in the same sample. According to the present invention, the sample comprising the microbes may be a biological sample, environmental sample, an artificially created sample (e.g., a laboratory test or control sample, a sample of a probiotic composition or supplement, etc.), or the like. Examples of biological samples include tissue samples, blood samples, plasma samples, cerebrospinal fluid samples, urine samples, fecal samples, samples of material obtained from the digestive tract, biological secretions (e.g., semen, vaginal secretions, breast milk, tears, saliva, etc.), and the like. Solid samples may be liquefied or mixed with a solution, and then genetic material of the microbes present in the liquefied sample, mixture, or solution obtained from the mixture may be extracted in accordance with the present invention. The extracted genetic material may be subjected to further processing and analysis such as purification, amplification, and sequencing.

In some embodiments, the extracted genetic material is subjected to metagenomics analysis to, for example, identify the one or more types of microbes in the sample from which the genetic material was extracted. In additional embodiments, full whole genome shotgun sequencing can be performed on prepared extracted nucleic acid material from human fecal samples. Preparations include nucleic acid clean up reactions to remove organic solvents, impurities, salts, phenols, and other process inhibiting contaminants. Additional preparations include nucleic acid library prep from each sample where the gDNA is subject to modifications and/or amplifications to prep the sample for sequencing on a sequencing platform such as massively parallel sequencing by synthesis, nanopore, long read, and/or CMOS electronic, sequencing methods.

As disclosed herein, the inventive method allows the successful extraction of genetic material from one or more different types of microbes present in the same sample by subjecting the microbes to three different compositions in a particular order. The method according to the present invention comprises first lysing any gram-negative bacteria present in the sample, which is followed by digesting the polysaccharide component of the cell walls of any yeast and bacteria present in the sample, and then disrupting any cell walls that are intact after the second step with a chaotropic agent.

Briefly, in an embodiment, the first step comprises mixing the sample with a first lysis solution comprising a detergent (e.g., sodium dodecyl sulfate (SDS)) and a chelator (e.g., ethylenediaminetetraacetic acid (EDTA)) to lyse any gram-negative bacteria present in the sample. The first lysis solution may further include one or more buffers (e.g., Tris), one or more mild detergents (e.g., Triton™ X-100), and/or one or more proteases (e.g., proteinase K).

After the first step, the sample is mixed with a second lysis solution comprising a lysozyme to digest the polysaccharide component of any yeast and bacterial cell walls present in the mixture. Because lysozyme may inhibit the activity of the first lysis solution, it is important that contact of the sample with the second lysis solution occurs after treating the sample with the first lysis solution.

After treatment with the second lysis solution, a third lysis solution comprising a chaotropic agent (e.g., urea, lithium acetate, guanidine hydrochloride, and the like) is added to the mixture to disrupt any cell walls that are not digested by the second lysis solution. The third lysis solution may include a detergent such as SDS.

In some embodiments, both the first lysis solution and the third lysis solution comprise SDS at a working concentration of between 1-10% w/v. In some embodiments, after treatment with the third lysis solution, the mixture is further treated with a fourth lysis solution comprising a chaotropic agent (e.g., urea, lithium acetate, guanidine hydrochloride, and the like) and Proteinase K. In some embodiments where the chaotropic agent of the third lysis solution is lithium acetate, the mixture is then subjected to heat shock treatment and may then be treated with the fourth lysis solution.

In certain aspects, the following disclosure describes a universal method for using stool samples for DNA extraction and determination of food consumption based on food DNA sequence from a database of meats, plants, fruits, vegetables, and/or microbes contained with these organisms. Disclosed herein are methods of extracting genetic material from a diverse population of one or more types of cells or cell components in a sample and determining the consumed food and nutritional breakdown for the improvement of health and prevention of disease.

In some embodiments, biological secretions (e.g., semen, vaginal secretions, breast milk, tears, saliva, blood, urine, and the like) are obtained from the digestive tract, and the like. Solid samples may be liquefied or mixed with a solution, and then genetic material of any food item containing genetic material, such as plant based (seedlings, leaves, cotyledons, seeds, endosperm, tissue culture callus, roots, and the like), animal based, fungi based, or protista based foods in the liquefied sample, mixture, or solution obtained from the mixture may be extracted in accordance with the present invention or other standard nucleic acid extraction protocols known in the art. In some embodiments, the extracted genetic material may be subjected to further processing and analysis, such as purification, amplification, and sequencing. In some embodiments, the extracted genetic material is subjected to metagenomics analysis to, for example, identify the one or more types of organisms in the sample from which the genetic material was extracted.

In some embodiments the database that the metagenomic analysis will utilize has been customized for a specific purpose of identifying and taxonomically assigning, within the appropriate phylogeny, the nucleic acids with relative abundances of organisms or components of organisms ingested by humans or other animals. In some embodiments and additional data table or database may be used as a lookup of the relative abundances of organisms to determine macronutrient content of an organism's gut sample as a representation of their diet. In some embodiments this macronutrient breakdown may include fats, carbohydrates, proteins, vitamins minerals, and subcomponents of any macronutrients.

As disclosed herein, the inventive method allows the successful extraction of genetic material from one or more different types of organisms, one or more of an organism's cells, or cellular matrices or organelles present in the same sample by subjecting the sample to isolation, purification, or other methods for capturing nucleic acids. The method according to the present invention comprises lysing or disrupting any food cells in the sample, including but not limited to any cell walls and cell membranes, digesting the polysaccharide or lignin component of any cell walls or membranes of any fungi, plant, mammalian, or protista cells present in the sample, and disrupting any cell walls that are intact after the digestion step with a chaotropic agent.

The present invention includes a step to physically disrupt the cell wall or membranes of food cells by liquid nitrogen flash freezing and immediate mechanical disruption or grinding to break down cell walls and keep harmful cell enzyme inactivated prior to chemical lysis. The present invention includes a step comprising mixing the sample with a first lysis solution comprising a detergent (e.g., sodium dodecyl sulfate (SDS)) and a chelator (e.g., ethylenediaminetetraacetic acid (EDTA)) to lyse any animal cells present in the sample. The first lysis solution may further include one or more buffers (e.g., Tris), one or more mild detergents (e.g., Triton™ X-100, Cetyltrimethylammonium bromide), and/or one or more proteases (e.g., proteinase K). In particular embodiments, the first lysis solution comprises SDS at a working concentration 1-10% w/v. The present invention includes a step comprising mixing the sample with a second lysis solution comprising a chaotropic agent (e.g., urea, lithium acetate, guanidine hydrochloride, and the like). The second lysis solution may include a detergent, such as SDS. In particular example embodiments, the first and second lysis solutions may be added in any particular order.

In some embodiments, the present invention may include a step comprising mixing the sample with a third lysis solution comprising a lysozyme to digest the polysaccharide component of any fungi or bacteria cell walls present in the mixture. In some embodiments, the mixture may be further treated with a fourth lysis solution comprising a chaotropic agent (e.g., urea, lithium acetate, guanidine hydrochloride, and the like) and Proteinase K. In some embodiments where the chaotropic agent of the fourth lysis solution is lithium acetate, the mixture may then be subjected to heat shock treatment and may then be treated with the fourth lysis solution. In particular example embodiments, the third and/or fourth solution may be added to the mixture at any point to disrupt any cell walls that are not digested by any previous lysis solution.

In some embodiments, if the sample has or is suspected of having bacterial and/or fungal spores, the sample may be subjected to a pretreatment step that induces germination of the cell walls of the spores before contact with the first lysis solution. The pretreatment step may comprise mixing the sample with a chemical such as a mild detergent, e.g., Tween-80, to induce germination or cultivating the sample under conditions (e.g., temperature) that induce germination. In some embodiments, where germination is induced with a chemical, the chemical is preferably one that does not inhibit, reduce, or modify the activity or effectiveness of the first, second, and third lysis solutions.

In some embodiments, the method according to the present invention may further include one or more mechanical treatment steps that cause physical lysis by mechanical methods including sonication, bead mixing, bead mill homogenization, pressurization, microfluidization, and the like. In some embodiments, a mechanical treatment step is performed before subjecting the sample to the first lysis solution.

In embodiments, the method according to the present invention is capable of extracting nucleic acid molecules from a variety of microbes including yeast (i.e., *Saccharomyces* spp.), gram-negative bacteria (e.g., *Acinetobacter* spp.), gram-positive bacteria (e.g., *Bifidobacterium* spp.), viruses (e.g., *Sclerotinia* spp.), spores (*Bacillus* spp.) Helminths (tapeworm *Echinococcus* spp.), Protozoa (Sarcodina—the ameba, e.g., *Entamoeba*) and phages (e.g., *Lactobacillus* phages).

In embodiments, the method according to the present invention is capable of extracting nucleic acid molecules from a variety of organisms including fungi (i.e., *Saccharomyces* spp.), animal cells (*Bos taurus*), plants (e.g., *Hordeum vulgare*).

The following examples are intended to illustrate but not to limit the invention.

Extraction Method A

A range of 10 mg to 5000 mg of sample were added to a sterile 2 milliliters (mL) micro centrifuge tube. Bead beating may optionally be performed by adding 400 microliters (µL) of bead pure mixture and vortexing for about 30 seconds at 8000 rpm. If, however, high-molecular weight nucleic acids, e.g., genomic DNA, are desired to be obtained, bead beating is preferably avoided.

First Lysis Solution Treatment Step

To lyse any gram-negative bacteria in the sample, the sample was subjected to a First Lysis Solution by adding about 400 µL of Digestion Buffer (1% w/v SDS, 25 mM Tris HCl, 2.5 mM EDTA, 1% Triton™ X-100, pH 8) and about 20 µL of Proteinase K to the sample and gently mixed. The mixture was then incubated for about 30 minutes at 55° C.

Second Lysis Solution Treatment Step

To lyse any gram-positive bacteria in the sample, a Second Lysis Solution comprising a glucoside hydrolase ("lysozyme") was added to the mixture obtained from the First Lysis Solution Treatment Step to give a final lysozyme concentration of 1 mg/mL and a pH of about 8.0. Suitable glucoside hydrolases may be obtained from a variety of sources including egg whites, tears, or mucus or saliva of various animals. The mixture was then incubated for a period of about 1 to 24 hours at 37° C.

Third Lysis Solution Treatment Step

To lyse any fungal and/or yeast cells present in the sample, a Third Lysis Solution comprising 1M lithium acetate in distilled sterile H2O and 5% w/v SDS was added to obtain about a 1:5 dilution of the mixture resulting from the Second Lysis Solution Treatment Step. The treated mixture was incubated for 15 minutes at 70° C. followed by heat shock at 95° C. for one minute and then brought to room temperature by placing in a 22° C. water bath.

As the Second and Third Lysis Solution Treatment Steps are sufficient to lyse the outer coats of bacteriophages and viruses, no additional step is needed for extracting the genetic material from bacteriophages and viruses that may be present in the sample.

Extraction Method B

Pre-Lysis Treatment Step 100-200 mg of sample were added to a sterile 2 milliliters (mL) micro centrifuge tube. Add 500 mL of liquid nitrogen and allow sample to freeze for 30 sec. Then using a pellet pestle or saw-tooth generator probe, grind the sample thoroughly before continuing to the next step.

First Lysis Solution Treatment Step

To lyse any animal, fungi, and protista food cell membranes in the sample, the sample was subjected to a First Lysis Solution by adding about 400 μL of Digestion Buffer (1% w/v SDS, 25 mM Tris HCl, 2.5 mM EDTA, 1% Triton™ X-100, 1.2M NaCl pH 8) and about 20 μL of Proteinase K to the sample and gently mixed. The mixture was then incubated for about 30 minutes at 55° C.

Second Lysis Solution Treatment Step

To lyse any fungal and/or yeast cells present in the sample, a second Lysis Solution comprising 1M lithium acetate in distilled sterile H2O and 5% w/v SDS was added to obtain about a 1:5 dilution of the mixture resulting from the first lysis solution treatment step. The treated mixture was incubated for 15 minutes at 70° C. followed by heat shock at 95° C. for one minute and then brought to room temperature by placing in a 22° C. water bath.

Nucleic Acid Purification

In an embodiment, the genetic material extracted from the lysed microbes, i.e., the nucleic acid molecules present in the mixture after being subjected to the First, Second, and Third Lysis Solution Treatment Steps were then purified to DNA and RNA purification by splitting the mixture into two microcentifuge tubes. DNA was extracted from one tube by adding about 20 μL RNAse A and incubating for 5 minutes at room temperature. The mixture was run through a biopolymer tissue homogenizer column. If bead beating was previously performed, subjecting the mixture to the tissue homogenizer column is preferably avoided.

The eluate was then centrifuged at 1000 g for 5 minutes. The supernatant was treated with about 400 μL of DNA Lysis Solution (Guanidine HCl, Tris-EDTA, and 70% EtOH) and about 20 μL of Proteinase K, mixed, and then incubated at 55° C. for 10 minutes. Then EtOH at −22° C. was added and the mixture was mixed by inverting. The mixture may be subjected to one or more additional DNA extraction and purification methods known in the art.

RNA was extracted from the second microcentrifuge tube by running the mixture through a biopolymer tissue homogenizer column. Again, if bead beating was previously performed, subjecting the mixture to the tissue homogenizer column is preferably avoided. The eluate was then centrifuged at 1000 g for 5 minutes. The supernatant was treated with about 40 μL DNase I (1 U) in a solution of 25 mM MgCl2 and then incubated at 37° for about 15 minutes. Then the mixture was subjected to acid guanidinium thiocyanate-phenol-chloroform extraction. The mixture may be subjected to one or more additional RNA extraction and purification methods known in the art.

In an embodiment, the genetic material extracted from the lysed microbes, i.e., the nucleic acid molecules present in the mixture after being subjected to the First, Second, and pre lysis Treatment Steps were then purified to DNA and RNA purification by splitting the mixture into two microcentifuge tubes. DNA was extracted from one tube by adding about 20 ?L RNAse A and incubating for 5 minutes at room temperature.

The eluent was then centrifuged at 1000 g for 5 minutes. The supernatant was treated with about 400 μL of DNA Lysis Solution (Guanidine HCl, Tris-EDTA, and 70% EtOH) and about 20 μL of Proteinase K, mixed, and then incubated at 55° C. for 10 minutes. Then EtOH at −22° C. was added and the mixture was mixed by inverting. The mixture may be subjected to one or more additional DNA extraction and purification methods known in the art.

RNA was extracted from the second microcentrifuge tube. The eluent was then centrifuged at 1000 g for 5 minutes. The supernatant was treated with about 40 μL DNase I (1 U) in a solution of 25 mM MgCl2 and then incubated at 37° for about 15 minutes. Then the mixture was subjected to acid guanidinium thiocyanate-phenol-chloroform extraction. The mixture may be subjected to one or more additional RNA extraction and purification methods known in the art.

In some embodiments, where the quantitative expression of RNA molecules is desired, the use of an RNA stabilization buffer and bead beating is preferred to ensure release and limited degradation of RNA nucleic acid molecules.

In some embodiments where extraction of high molecular weight nucleic acid molecules is desired, bead beating and tissue homogenization column are avoided and phenol-chloroform-alcohol extraction is performed instead of silica column based extraction. In some embodiments a magnetic bead based nucleic acid purification may be performed. To remove selective molecular weights of nucleic acids and purify the sample, an agarose gel based purification and enrichment may be performed.

Metagenomics Analysis

In an embodiment, the extracted and purified genetic material was prepared for sequencing using Illumina index adaptors and checked for sizing and quantity. Low cycle PCR was performed between 1-20 cycles for any input less then 50 ng of DNA, otherwise PCR-Free methods of library prep can be utilized for 50 ng of nucleic acid or greater. Gel purification was performed using the Qiagen Gel Purification Kit™ (Qiagen, Frederick, MD). Clean PCR products were quantified using the Qubit™ 2.0 Fluorometer (Life Technologies, Carlsbad, CA). Samples were combined in equimolar amounts. Library pools were size verified using the Fragment Analyzer™ CE (Advanced Analytical Technologies Inc., Ames IA) and quantified using the Qubit™ High Sensitivity dsDNA kit (Life Technologies, Carlsbad, CA). After dilution, a 1% to 10% spike of PhiX™ V3 library control (Illumina, San Diego CA), pools were denatured for 5 minutes in an equal volume of 0.1 N NaOH then further diluted in Illumina's HT1 buffer. The denatured and PhiX™-spiked pool was loaded on an Illumina Next Generation™ Sequencer with Illumina sequencing primers and set for between 50-550 base, paired-end or single reads.

A range from 1000 or greater reads of sequencing for short insert methods can be used for this method. Large insert methods such as Pac Bio™, Nanopore™, or other next gene sequencing methods can use <1000 sequencing reads. Bioinformatics quality filtering was performed before taxonomy assignment. Quality trimming of raw sequencing files may include removal of sequencing adaptors or indexes; trimming 3' or 5' end of reads based on quality scores (Q20>), basepairs of end, or signal intensity; removal of reads based on quality scores, GC content, or non-aligned basepairs; removal of overlapping reads at set number of base pairs. Alignment of processed sequencing files was done using a custom microbial genome database consisting of sequences from Refseq™, Greengeens™, HMP™ NCBI™, PATRIC™, or other public/private data repositories or in-house data sets. This database may be used as full genome alignment scaffold, k-mer fragment alignment, or other schemes practiced in the art of metagenomics and bioinformatics. Based off the number of sequencing reads/fragments that match the database genomes we assign a taxonomic identity that is common or unique to the organism. This identifier can be a barcode, nucleotide sequence, or some other computational tag that will associate the matching sequencing read to an organism or strain within a taxonomic group. Some identifiers will be of higher order and would identify domain, kingdom, phylum, class, order, family, or genus of the organism.

The present invention is able to identify the organism at the lowest order of strain within a species.

In embodiments the invention includes identification and/or analysis of one or more bacteria contained within our database (FIG. 10). Some selected examples are *Bacillus clausii*, *Bifidobacterium animalis*, *Pediococcus acidilactici*, *Acinetobacter indicus*, *Lactobacillus salivarius*, *Acinetobacter*, *Bacillus amyloliquefaciens*, *Lactobacillus helveticus*, In an embodiment, the extracted and purified genetic material was prepared for sequencing using Illumina index adaptors and checked for sizing and quantity. Low cycle PCR may be performed or standard PCR-free methods. Gel purification was performed using the Qiagen Gel Purification Kit™ (Qiagen, Frederick, MD). Clean PCR products were quantified using the Qubit™ 2.0 Fluorometer (Life Technologies, Carlsbad, CA). Samples were combined in equimolar amounts. Library pools were size verified using the Fragment Analyzer™ CE (Advanced Analytical Technologies Inc., Ames IA) and quantified using the Qubit™ High Sensitivity dsDNA kit (Life Technologies, Carlsbad, CA). After dilution, a 10% spike of PhiX™ V3 library control (Illumina, San Diego CA), pools were denatured for 5 minutes in an equal volume of 0.1 N NaOH then further diluted in Illumina's HT1 buffer. The denatured and PhiX™-spiked pool was loaded on an Illumina™ Next Generation Sequencer with Illumina sequencing primers and set for 150 base, paired-end reads. Bioinformatics quality filtering was performed before taxonomy assignment.

Using Table 1, we determine that the individual has consumed the following:

TABLE 1

| Taxon Level | Reference ID | Species Name | reads_subtree | reads_subtree_reestimated | abundances_subtree | abundances_subtree_reestimated |
| --- | --- | --- | --- | --- | --- | --- |
| S | 4513 | *Hordeum vulgare* | 684758 | 651478 | 4.56 | 77.33 |
| S | 9858 | *Capreolus capreolus* | 1522 | 1522 | 0.09 | 11.10 |
| S | 3276 | *Raphanus sativus* | 179566 | 179566 | 10.21 | 36.03 |
| S | 161934 | *Beta vulgaris* | 3251 | 0 | 0.17 | 11.21 |
| S | 4565 | *Triticum aestivum* | 32243 | 32243 | 1.24 | 32.47 |
| S | 93759 | *Corchorus olitorius* | 23293 | 23293 | 0.15 | 18.56 |
| S | 9796 | *Equus caballus* | 69875 | 69875 | 0.43 | 11.49 |
| S | 4120 | *Ipomoea batatas* | 5374 | 5374 | 0.13 | 11.71 |

*Bacillus subtilis*, *Lactobacillus plantarum*, *Bifidobacterium longum* subsp *infantis*, *Enterococcus hirae*, *Lactobacillus delbrueckii* subsp *bulgaricus*, *Enterococcus*, *Lactobacillus rhamnosus*, *Lactococcus lactis*, *Pseudomonas stutzeri*, *Lactobacillus acidophilus*, *Klebsiella* and *Enterobacter cloacae* strain.

In embodiments the invention includes identification and/or analysis of one or more yeast contained within our database (FIG. 10). Some selected examples are *Saccharomyces* sp. *Boulardii*, *Saccharomyces kudriavzevii*, *Saccharomyces pastorianus* and *Saccharomyces cerevisiae*.

In embodiments the invention includes identification and/or analysis of one or more phage or viruses contained within our database (FIG. 10). Some selected examples are *Bacillus* phage phi29, Enterobacteria phage HK022, *Lactobacillus* phage A2, *Escherichia* phage HK639, Phage cdtI, *Sclerotinia sclerotiorum* partitivirus S segment 2, *Burkholderia* phage BcepMu, *Lactococcus* prophage bIL311, *Enterococcus* phage phiFL4A and *Streptococcus* phage SM1.

Future database improvements will increase or refine the organisms that can be detected by this method.

Monitoring Macronutrient Intake and Dietary Guidance

In some embodiments, the present invention may be used to monitor food intake nutrition, quantity, and quality in subjects. For example, prior to treatment with a probiotic, a sample obtained from the digestive tract of a subject may be obtained and the genetic material of the food organisms therein extracted as disclosed herein and subjected to metagenomics analysis. A customized food specific database comprised of whole, partial, or incomplete reference genomes, RNA's, or nucleic acid components or fragments will be utilized by bioinformatics tools to identify, quantify, and taxonomically assign the nucleic acid information from sequencing. The output of which is exemplified in Table 2 below and contains identification of the species of organisms or cells of organisms that were in the gut.

TABLE 2

| Scientific Name | Common Name | Relative Abundance | In Grams | | | As a percent of daily recommended | | | | |
|---|---|---|---|---|---|---|---|---|---|---|
| | | | Fats | Carbs | Proteins | Iron | Vitamin A | Vitamin B | Vitamin C | Vitamin D |
| Capreolus capreolus | Deer | 0.05 | 2.7 | 0 | 26 | 21.0% | | | | |
| Raphanus sativus | Raddish | 0.05 | 0 | 0.2 | 0 | 0.0% | 10.0% | | | |
| Beta vulgaris | Beet | 0.05 | 0.2 | 13 | 2.2 | 6.0% | 5.0% | 11.0% | | |
| Triticum aestivum | Wheat | 0.3 | 4.7 | 137 | 26 | 37.0% | 40.0% | | | |
| Corchorus olitorius | Jute | 0.05 | 0.2 | 0 | 6 | 15.0% | 90.0% | 25.0% | 47.0% | |
| Bos taurus | Cattle | 0.4 | 6 | 0 | 22 | 15.0% | | | | |
| Ipomoea batatas | Sweet Potato | 0.1 | 0.1 | 27 | 2.1 | 4.0% | 377.0% | 15.0% | 5.0% | |

Then during and/or after treatment with a given probiotic, a second sample may be obtained from the digestive tract of the subject and the genetic material of the microbes in the second sample extracted and subjected to metagenomics analysis, the results of which are compared to the results of the metagenomics analysis of the first sample. Then, based on the comparative results, the food organism results may be compared to the microbiome organism results to understand the microbes associated with food and an overall food quality assessment. In some embodiments, this may provide information to the species of organism that an individual is ingesting through their food source and any genetic modifications, mutations, or irregularities to the species either by selection or direct modification.

In some embodiments, the second sample of microbiome analysis will enable detection of microbes common to the food organisms and provide information on the health of the food organism. In some embodiments, the human consumed food may be part of the common food source such as chickens, cows, pig, or even plants, and protista where the species will be identified and match to microbes that are specific to them. In particular example embodiments, a chicken species that may have a chicken sarcoma virus may be detected in the second gut microbiome sample analyzed. In some embodiments, the health of a food organism ingested can be determined by the presence or absence of microbes that negatively impact the health of the host organism. In particular example embodiments, a disease, such as Equid herpesvirus 2, which is a respiratory disease in horses, may be detected that may impact the health of a host organism.

In some embodiments, the present invention may be used to screen the gut microbiome of a given subject and then custom tailor a food or diet regime that would enable them to improve the quality of their health for aspects of nutritional balance, improved microbial gut profile, and absorption of nutrients.

Monitoring Probiotic Treatment

In some embodiments, the present invention may be used to monitor probiotic treatment in subjects. For example, prior to treatment with a probiotic, a sample obtained from the digestive tract of a subject may be obtained and the genetic material of the microbes therein extracted as disclosed herein and subjected to metagenomics analysis. Then during and/or after treatment with a given probiotic, a second sample may be obtained from the digestive tract of the subject and the genetic material of the microbes in the second sample extracted as disclosed herein and subjected to metagenomics analysis, the results of which are compared to the results of the metagenomics analysis of the first sample. Then, based on the comparative results, the probiotic treatment of the subject may be modified to obtain a desired population of microbes in the gut of the subject. For example, a probiotic that comprises a microbe whose amount is desired to be increased in the gut of the subject may be administered to the subject.

In some embodiments, the fecal sample may be mixed or cultured for determination of metabolomic of microbial fecal community. Metabolomic profile can then be used to determine probiotic strains that would benefit the individual. Examples of metabolomic profiles include those affecting energy metabolism, nutrient utilization, insulin resistance, adiposity, dyslipidemia, inflammation, short-chain fatty acids, organic acids, cytokines, neurotransmitters chemicals or phenotype and may include other metabolomic markers.

Microbiome Screening and Probiotic Selection

The present invention has been successfully used to determine the microbe content of a variety of commercially available probiotics. Additionally, the methods of the present invention are used to determine the microbe content of various probiotics and the microbiome content in the gut of the subject. In one embodiment, based on the microbiome content in the gut of the subject and any desired changes thereto, one may select one or more probiotics that contain the microbes that are desired to be increased and/or maintained in the subject's microbiome health. In one embodiment, based on the microbiome content in the gut of the subject and any desired changes thereto, one may select one or more probiotics that contain the microbes that are desired to be increased and/or maintained in the subject's gut balance in relation to the macronutrient content they are getting from their food source as recorded by survey information from the individual directly or by the present invention of gut organism nucleic acid analysis.

Where the microbiome represents a full picture of their microbiota and the organisms contained in them from bacteria, fungi, viruses, phages, and parasites. For example, using the methods described herein, a subject's gut microbiome is determined to contain 25% A and 75% B, Probiotic 1 is determined to contain 75% A and 25% B and Probiotic 2 is determined to contain 25% A and 75% B. If the subject's gut microbiome is desired to be maintained, one would select Probiotic 2 for administering to the subject. However, if the amounts of A and B in the subject's gut are desired to be 50/50, one may select both Probiotics 1 and 2 to be administered to the subject. Alternatively, one may select Probiotic 1 to be administered to the subject until the amounts of A and B in the subject's gut reaches 50/50. In some embodiments, one may custom tailor a probiotic formulation, e.g., containing equal, varying, or diverse amounts of A and B or other probiotic strains, for administration to the subject. Calculation models utilizing relative abundance of the microbes present in an individual's gut will help determine the type, dose, and cocktail of microbes to include in the probotic. For example, if it is determined that organism A is reduced or absent compared to the general population or previous microbiome analysis, then we would provide probiotic or prebiotics that would increase the concentration of organism A. This prebiotic or probiotic may be the exact organism A or another organism what would support the grown of organism A. The dose given would consider relative abundance of organisms in the individual, performance characteristics of the prebiotic/probiotic such as growth rate, compatibility, receptors or receptor density, genes, or expression patterns, or metabolomic products.

Custom tailored probiotics may not be in equal amounts but are formulated based on relative abundance detected from the individual gut/fecal sample. These formulations are geared to modulate the microbiome to a healthy status. The healthy status of a microbiome is determined by the use of existing aggregate private and public databases such as metaHIT™, Human Microbiome Project™, American Gut Project™, and the like. The healthy status may also be determined individually when a person has no known issues and is in good health, from a blood biomarker checkup perspective, and then has their full microbiome profile completed. After one or several microbiome signatures have been completed then the average of some/all of the microbes found can be understood for that individual and variances from that average can be accessed to determine if they are in dysbiosis. Microbiome profiles can be aggregated into groups that are then assigned a barcode for rapid bioinformatic assignment. Groups can be created by single or multiple phenotypic, diagnostic, or demographic information related to the individual from which the sample was collected from. A unique group can be determined from another group by using statistical models such as linear distance calculations, diversity values, classifiers such as C4.5 decision tree, or principal component analysis an comparing to an aggregate known population such as "normals" defined by the Human Microbiome Project or American Gut Project.

Thus, in some embodiments, the present invention may be used to screen the gut microbiome of a given subject and then custom tailor a probiotic regimen to the given subject based on the subject's gut microbiome.

Treatment of Dysbiosis

In some embodiments, the present invention may be used to restore a subject's gut flora and/or fauna to homeostasis after an event that has caused a shift in the subject's microbiota from balanced microbiome to one that is causing or may be causing negative side effects, disorders, and/or disease. Health conditions can include but is not limited to various conditions, from acne and allergies, through gastrointestinal ailments, obesity and cancer. One example of such a dysbiosis is in the case of the onset of obesity. Several strains of microbes in the guts of subjects have been shown to be associated with obesity or weight management issues suffered by the subjects. See, e.g., Ley, et al. (2005) PNAS USA 102:11070-11075. For example, in obese animal and human subjects, the ratio of Bacterides to Firmicutes phyla microbes plays an important role in metabolic performance See, e.g., Turnbaugh, et al. (2012) PLOS ONE 7:e41079. Some gut microbes known to be associated with obesity and weight management issues include *Bacteroides uniformis*, *Bacteroides pectinophilus*, *Roseburia inulinivorans*, *Methanobrevibacter smithii*, and *Bifidobacterium animalis*.

Thus, in some embodiments, a ratio of a first given microbe to a second given microbe in the gut of a subject is determined using the methods described herein and then if the ratio is undesired or abnormal, the subject is administered a treatment to modify the ratio to be a desired ratio. In some embodiments, the amount of a first given microbe in a gut of a subject relative to the total amount of all the microbes in the gut of the subject is determined using the methods described herein and then if the relative amount of the first given microbe is undesired or abnormal, the subject is administered a treatment to modify the amount to be a desired amount. Re-testing of their gut microbiome may be used to determine well they are adhering to the macronutrient and food guidance. Such treatments include administering to the subject: a probiotic containing one or more microbes whose amounts are desired to be increased in the gut of the subject, an antimicrobial agent, e.g., an antibiotic, an antifungal, an antiviral, etc., to kill or slow the growth of a microbe or microbes whose amounts are desired to be decreased in the gut of the subject, a diet and/or a dietary supplement that supports the growth or maintenance of a healthy gut microbiome, e.g., a prebiotic, magnesium, fish oil, L-glutamine, vitamin D, etc., and the like. For example, Million, et al. ((2005) Int. J. Obes. 36:817-825) indicate that the gut microbiota of obese subjects are enriched in *Lactobacillus reuteri* and depleted in *Bifidobacterium animalis* and *Methanobrevibacter smithii*. Therefore, after determining the amounts of *Lactobacillus reuteri*, *Bifidobacterium animalis*, and *Methanobrevibacter smithii* in the gut of a subject using the methods described herein and finding that the amounts are typical or indicative of obesity-associated gut microbiota, the subject may be administered a probiotic containing *Bifidobacterium animalis* and *Methanobrevibacter smithii* and relatively little to no amount of *Lactobacillus reuteri*. In embodiments, the gut microbiota of obese subjects would benefit from foods with flavonoids, polyphenols, and short chain fatty acids.

Scoring of Your Microbiome

Scoring of the microbiome signature overall uses a similar decision tree, algorithm, artificial intelligence, script, or logic tree as represented in Table 3. This system would enable a score that helps a user understand how healthy their gut microbiome is and if they need to take action on a few or many challenges found. Challenges can include but not limited to, identification of known pathogenic organisms, count and identification of opportunistic pathogens, latent organisms known to cause pathogenic affects when given opportunity, lack of support for good microbial environment but their composition or lack of key strains, overall diversity and count of unique organisms found in top 10 and or organisms with greater than 0.1% prevalence.

Diversity cut offs were determined from an aggregate of sample analysis and a cutoff is determined at x relative abundance. For example, if x=0.1% then 352 unique organisms make up the average healthy profile. Then apply standard deviations around this number and using a Gaussian distribution and percentile under the curve analysis we can score how close to the average diversity number from our database average. The lower your diversity number and further away from the average you are then the less that microbiome would score. The higher the number and the greater your diversity is the more that microbiome would score. This type of scoring categories along with probiotic score will determine a number and visual metered score for the custom to understand how healthy their microbiome is. An example of the graphic visualization is included below.

Where low is equal to low microbiome quality and high is equal to high microbiome quality and score. Low→30 out of 100, Med→65 out of 100, High=65 or greater out of 100.

An example of a scoring and probiotic formula algorithm is included in Table 3 below. Table 3 can be represented as decision tree, algorithm, artificial intelligence, script, or logic tree. The function of such decision tree, algorithm, artificial intelligence, script, or logic tree would be output a score of wellness of the individual microbiome as related to probiotics detected and to provide formulation and dosing recommendations for probiotic usage.

An exemplary list of potential categories into which microbes may be grouped is set forth in Table 4 below.

TABLE 3

Example Decision Table for Probiotic Scoring and Formulation.
Includes the Utilization of a Probiotic Strain Database,
Metagenomic Analysis Database, and Literature Curation Database

| Criteria Number | Criteria | Criteria Answer | Score or Inclusion/Exclusion |
|---|---|---|---|
| 1 | Greater than 100 reads | Yes | If yes then include |
| 2 | Greater than 50% of total probiotic reads | Yes | |
| 3 | Greater than 10,000 reads | Yes | If yes do not include in probiotic formula |
| 4 | Greater than 50% of total reads | No | |
| 5 | Greater than 30,000 reads | Yes | If yes do not include in probiotic formula |
| 6 | Greater than 30,000 reads for x number of probiotics | Yes | If x > 5 then score + 20, x > 3 score 10, x > 1 score 5 |
| 7 | Total number of microbes above 100 reads (count) | x | If x > 10 then score + 20, x > 10 then score 10, x > 5 score 5 |
| 8 | Query for probiotic strains and output where 1 = yes and 4 is no and 6 is no and the number of reads is less than 1000 | Yes | Include in formula at 20 CFU/g or greater |
| 9 | If *bacillus* | Yes | Do not include |
| 10 | If *lactobacillus acidophilus* greater than x reads | Yes | If x > 10000 score + 20, if x > 1000 score + 10, if x > 100 score + 5 |
| 11 | If *bacillus* genus greater than x reads | Yes | If x > 1000 score + 20, if x > 100 score + 10, if x > 10 score + 5 |
| 12 | If *Saccharomyes boulardi* greater than x reads | Yes | If x > 1000 score + 20, if x > 100 score + 10, if x > 10 score + 5 |
| 13 | If infant if nursing and *bifidobacterium infantis* > x% | Yes | If x > 10 then score + 5, x > 30% then score + 10, x > 50% then score + 20, x > 70% then score + 30 |
| 14 | If not infant, not child and *bifidobacterium infantis* > x% | Yes | If x > 20 then score + 5, if x > 10 then score + 10, if x < 10 then score + 20 |
| 15 | Query to probiotic function, if function table is equal to health phenotype or healthDx then include in formula unless 3 or 5 = yes | | |

TABLE 4

Potential Categories from which to Create Groups

| Categories1 | Categories2 | Categories3 | Categories4 | Categories5 | Categories6 |
|---|---|---|---|---|---|
| ACID_REFLUX | FLOSSING_FREQUENCY | SCIENTIFIC_NAME | VIOSCREEN_D_YOGURT | VIOSCREEN_M_MEAT | VIOSCREEN_VITB12 |
| ACNE_MEDICATION | FLU_VACCINE_DATE | SEAFOOD_FREQUENCY | VIOSCREEN_EER | VIOSCREEN_M_MPF | VIOSCREEN_VITB6 |
| ACNE_MEDICATION_OTC | FROZEN_DESSERT_FREQUENCY | SEASONAL_ALLERGIES | VIOSCREEN_EMAIL | VIOSCREEN_M_NUTSD | VIOSCREEN_VITC |
| ADD_ADHD | FRUIT_FREQUENCY | SEQUENCING_METH | VIOSCREEN_ERYTHR | VIOSCREEN_M_ORGAN | VIOSCREEN_VITD |
| AGE_CAT | FUNGAL_OVERGROWTH | SEX | VIOSCREEN_FAT | VIOSCREEN_M_POULT | VIOSCREEN_VITD2 |
| AGE_CORRECTED | GEO_LOC_NAME | shannon_10k | VIOSCREEN_F_CITMLB | VIOSCREEN_M_SOY | VIOSCREEN_VITD3 |
| AGE_YEARS | GLUTEN | shannon_1k | VIOSCREEN_FIBER | VIOSCREEN_MULTI_CALCIUM_AVG | VIOSCREEN_VITD_IU |
| ALCOHOL_CONSUMPTION | HAS_PHYSICAL_SPECIMEN | SIBO | VIOSCREEN_FIBH2O | VIOSCREEN_MULTI_CALCIUM_DOSE | VIOSCREEN_VITE_IU |
| ALCOHOL_FREQUENCY | HEIGHT_CM | SKIN_CONDITION | VIOSCREEN_FIBINSO | VIOSCREEN_MULITVITAMIN | VIOSCREEN_VITK |
| ALCOHOL_TYPES | HEIGHT_UNITS | SLEEP_DURATION | VIOSCREEN_FINISHED | VIOSCREEN_MULITVITAMIN_FREQ | VIOSCREEN_V_ORANGE |
| ALCOHOL_TYPES_BEERCIDER | HIGH_FAT_RED_MEAT_FREQUENCY | SMOKING_FREQUENCY | VIOSCREEN_FISH_SERVINGS | VIOSCREEN_NATOCO | VIOSCREEN_V_OTHER |
| ALCOHOL_TYPES_RED_WINE | HOMECOOKED_MEALS_FREQUENCY | SOFTENER | VIOSCREEN_F_NJ_CITMLB | VIOSCREEN_NCCGLBR | VIOSCREEN_V_POTATO |
| ALCOHOL_TYPES_SOUR_BEERS | HOST_COMMON_NAME | SPECIALIZED_DIET | VIOSCREEN_F_NJ_OTHER | VIOSCREEN_NCCGLGR | VIOSCREEN_V_STARCY |
| ALCOHOL_TYPES_SPIRITSHARD_ALCOHOL | HOST_SUBJECT_ID | SPECIALIZED_DIET_EXCLUDE_DAIRY | VIOSCREEN_F_NJ_TOTAL | VIOSCREEN_NIACIN | VIOSCREEN_V_TOMATO |
| ALCOHOL_TYPES_UNSPECIFIED | HOST_TAXID | SPECIALIZED_DIET_EXCLUDE_NIGHTSHADES | VIOSCREEN_FOL_DEQV | VIOSCREEN_NIACINEQ | VIOSCREEN_V_TOTAL |
| ALCOHOL_TYPES_WHITE_WINE | IBD | SPECIALIZED_DIET_EXCLUDE_REFINED_SUGARS | VIOSCREEN_FOL_NAT | VIOSCREEN_NITROGEN | VIOSCREEN_WATER |
| ALLERGIC_TO | IBD_DIAGNOSIS | SPECIALIZED_DIET_FODMAP | VIOSCREEN_FOL_SYN | VIOSCREEN_NON_FRIED_FISH_SERVINGS | VIOSCREEN_WEIGHT |
| ALLERGIC_TO_I_HAVE_NO_FOOD_ALLERGIES_THAT_I_KNOW_OF | IBD_DIAGNOSIS_REFINED | SPECIALIZED_DIET_HALAAL | VIOSCREEN_FORMONTN | VIOSCREEN_NUTRIENT_RECOMMENDATION | VIOSCREEN_WGRAIN |
| ALLERGIC_TO_OTHER | IBS | SPECIALIZED_DIET_I_DO_NOT_EAT_A_SPECIALIZED_DIET | VIOSCREEN_F_OTHER | VIOSCREEN_OMEGA3 | VIOSCREEN_WHOLE_GRAIN_SERVINGS |
| ALLERGIC_TO_PEANUTS | INSTRUMENT_MODEL | SPECIALIZED_DIET_KOSHER | VIOSCREEN_FRIED_FISH_SERVINGS | VIOSCREEN_OXALIC | VIOSCREEN_XYLITOL |
| ALLERGIC_TO_SHELLFISH | KIDNEY_DISEASE | SPECIALIZED_DIET_MODIFIED_PALEO_DIET | VIOSCREEN_FRIED_FOOD_SERVINGS | VIOSCREEN_OXALICM | VIOSCREEN_ZINC |
| ALLERGIC_TO_TREE_NUTS | LACTOSE | SPECIALIZED_DIET_OTHER_RESTRICTIONS_NOT_DESCRIBED_HERE | VIOSCREEN_FRTS_DAY | VIOSCREEN_PANTOTHE | VITAMIN_B_SUPPLEMENT_FREQUENCY |
| ALLERGIC_TO_UNSPECIFIED | LAST_MOVE | SPECIALIZED_DIET_PALEO_DIET_OR_PRIMAL_DIET | VIOSCREEN_FRTSUMM | VIOSCREEN_PECTINS | VITAMIN_D_SUPPLEMENT_FREQUENCY |
| ALTITUDE | LAST_TRAVEL | SPECIALIZED_DIET_RAW_FOOD_DIET | VIOSCREEN_FRUCTOSE | VIOSCREEN_PFA182 | VIVID_DREAMS |
| ALZHEIMERS | LATITUDE | SPECIALIZED_DIET_UNSPECIFIED | VIOSCREEN_FRUIT_SERVINGS | VIOSCREEN_PFA183 | WATER_LOT |

TABLE 4-continued

Potential Categories from which to Create Groups

| Categories1 | Categories2 | Categories3 | Categories4 | Categories5 | Categories6 |
|---|---|---|---|---|---|
| ANONYMIZED_NAME | LEVEL_OF_EDUCATION | SPECIALIZED_DIET_WESTENPRICE_OR_OTHER_LOWGRAIN_LOW_PROCESSED | VIOSCREEN_F_TOTAL | VIOSCREEN_PFA184 | WEIGHT_CHANGE |
| ANTIBIOTIC_HISTORY | LIBRARY_CONSTRUCTION_PROTOCOL | STATE | VIOSCREEN_GALACTOS | VIOSCREEN_PFA204 | WEIGHT_KG |
| APPENDIX_REMOVED | LINKER | SUBSET_AGE | VIOSCREEN_GAMMTOCO | VIOSCREEN_PFA205 | WEIGHT_UNITS |
| ARTIFICIAL_SWEETENERS | LinkerPrimerSequence | SUBSET_ANTIBIOTIC_HISTORY | VIOSCREEN_GENDER | VIOSCREEN_PFA225 | WELL_DESCRIPTION |
| ASD | LIVER_DISEASE | SUBSET_BMI | VIOSCREEN_GENISTN | VIOSCREEN_PFA226 | WELL_ID |
| ASSIGNED_FROM_GEO | LIVINGWITH | SUBSET_DIABETES | VIOSCREEN_GLAC | VIOSCREEN_PFATOT | WHOLE_EGGS |
| AUTOIMMUNE | LONGITUDE | SUBSET_HEALTHY | VIOSCREEN_GLTC | VIOSCREEN_PHENYLAL | WHOLE_GRAIN_FREQUENCY |
| BarcodeSequence | LOWGRAIN_DIET_TYPE | SUBSET_IBD | VIOSCREEN_GLUCOSE | VIOSCREEN_PHOSPHOR | |
| BIRTH_YEAR | LUNG_DISEASE | SUGAR_SWEETENED_DRINK_FREQUENCY | VIOSCREEN_GLUTAMIC | VIOSCREEN_PHYTIC | |
| BMI | MASTERMIX_LOT | SUGARY_SWEETS_FREQUENCY | VIOSCREEN_GLYCINE | VIOSCREEN_PINITOL | |
| BMI_CAT | MEAT_EGGS_FREQUENCY | SURVEY_ID | VIOSCREEN_GLYCITN | VIOSCREEN_POTASS | |
| BMI_CORRECTED | MENTAL_ILLNESS | TARGET_GENE | VIOSCREEN_G_NWHL | VIOSCREEN_PROCDATE | |
| BODY_HABITAT | MENTAL_ILLNESS_TYPE | TARGET_SUBFRAGMENT | VIOSCREEN_GRAMS | VIOSCREEN_PROLINE | |
| BODY_PRODUCT | MENTAL_ILLNESS_TYPE_ANOREXIA_NERVOSA | TAXON_ID | VIOSCREEN_G_TOTAL | VIOSCREEN_PROTANIM | |
| BODY_SITE | MENTAL_ILLNESS_TYPE_BIPOLAR_DISORDER | TEETHBRUSHING_FREQUENCY | VIOSCREEN_G_WHL | VIOSCREEN_PROTEIN | |
| BOWEL_MOVEMENT_FREQUENCY | MENTAL_ILLNESS_TYPE_BULIMIA_NERVOSA | THYROID | VIOSCREEN_HEI2010_DAIRY | VIOSCREEN_PROTOCOL | |
| BOWEL_MOVEMENT_QUALITY | MENTAL_ILLNESS_TYPE_DEPRESSION | TITLE | VIOSCREEN_HEI2010_EMPTY_CALORIES | VIOSCREEN_PROTVEG | |
| BREASTMILK_FORMULA_ENSURE | MENTAL_ILLNESS_TYPE_PTSD_POSTTRAUMATIC_STRESS_DISORDER | TM1000_8_TOOL | VIOSCREEN_HEI2010_FATTY_ACIDS | VIOSCREEN_QUESTIONNAIRE | |
| CANCER | MENTAL_ILLNESS_TYPE_SCHIZOPHRENIA | TM300_8_TOOL | VIOSCREEN_HEI2010_FRUIT | VIOSCREEN_RECNO | |
| CANCER_TREATMENT | MENTAL_ILLNESS_TYPE_SUBSTANCE_ABUSE | TM50_8_TOOL | VIOSCREEN_HEI2010_GREENS_BEANS | VIOSCREEN_RETINOL | |
| CARDIOVASCULAR_DISEASE | MENTAL_ILLNESS_TYPE_UNSPECIFIED | TONSILS_REMOVED | VIOSCREEN_HEI2010_SEAFOODS_PLANT_PROTIENS | VIOSCREEN_RGRAIN | |
| CAT | MIGRAINE | TYPES_OF_PLANTS | VIOSCREEN_HEI2010_PROTIEN_FOODS | VIOSCREEN_RIBOFLA | |
| CDIFF | MILK_CHEESE_FREQUENCY | VEGETABLE_FREQUENCY | VIOSCREEN_HEI2010_REFINED_GRAINS | VIOSCREEN_SACCHAR | |
| CENSUS_REGION | MILK_SUBSTITUTE_FREQUENCY | VIOSCREEN_A_BEV | VIOSCREEN_HEI2010_SCORE | VIOSCREEN_SALAD | |
| CENTER_NAME | MULTIVITAMIN | VIOSCREEN_A_CAL | VIOSCREEN_HEI2010_SODIUM | VEGETABLE_SERVINGS | |
| CENTER_PROJECT_NAME | NAIL_BITER | VIOSCREEN_ACESUPOT | VIOSCREEN_HEI2010_VEG | VIOSCREEN_SATOCO | |
| chao1_10k | NON_FOOD_ALLERGIES | VIOSCREEN_ACTIVITY_LEVEL | VIOSCREEN_HEI2010_WHOLE_FRUIT | VIOSCREEN_SCF | |
| chao1_1k | NON_FOOD_ALLERGIES_BEESTINGS | VIOSCREEN_ADD_SUG | VIOSCREEN_HEI2010_WHOLE_GRAINS | VIOSCREEN_SCFV | |
| CHICKENPOX | NON_FOOD_ALLERGIES_DRUG_EG_PENICILLIN | VIOSCREEN_ADDSUGAR | VIOSCREEN_HEI_DRK_G_ORG_VEG_LEG | VIOSCREEN_SELENIUM | |
| | | | | VIOSCREEN_SERINE | |

TABLE 4-continued

Potential Categories from which to Create Groups

| Categories1 | Categories2 | Categories3 | Categories4 | Categories5 | Categories6 |
|---|---|---|---|---|---|
| CLINICAL_CONDITION | NON_FOOD_ALLERGIES_PET_DANDER | VIOSCREEN_ADSUGTOT | VIOSCREEN_HEI_FRUIT | VIOSCREEN_SFA100 | |
| COLLECTION_DATE | NON_FOOD_ALLERGIES_POISON_IVYOAK | VIOSCREEN_AGE | VIOSCREEN_HEIGHT | VIOSCREEN_SFA120 | |
| COLLECTION_MONTH | NON_FOOD_ALLERGIES_SUN | VIOSCREEN_ALANINE | VIOSCREEN_HEI_GRAINS | VIOSCREEN_SFA140 | |
| COLLECTION_SEASON | NON_FOOD_ALLERGIES_UNSPECIFIED | VIOSCREEN_ALCOHOL | VIOSCREEN_HEI_MEAT_BEANS | VIOSCREEN_SFA160 | |
| COLLECTION_TIME | observed_otus_10k | VIOSCREEN_ALCOHOL_SERVINGS | VIOSCREEN_HEI_MILK | VIOSCREEN_SFA170 | |
| COLLECTION_TIMESTAMP | observed_otus_1k | VIOSCREEN_ALPHACAR | VIOSCREEN_HEI_NON_JUICE_FRT | VIOSCREEN_SFA180 | |
| COMMON_NAME | OLIVE_OIL | VIOSCREEN_ALPHTOCE | VIOSCREEN_HEI_OILS | VIOSCREEN_SFA200 | |
| CONSUME_ANIMAL_PRODUCTS_ABX | ONE_LITER_OF_WATER_A_DAY_FREQUENCY | VIOSCREEN_ALPHTOCO | VIOSCREEN_HEI_SAT_FAT | VIOSCREEN_SFA220 | |
| CONTRACEPTIVE | ORIG_NAME | VIOSCREEN_ARGININE | VIOSCREEN_HEI_SCORE | VIOSCREEN_SFA40 | |
| COSMETICS_FREQUENCY | OTHER_SUPPLEMENT_FREQUENCY | VIOSCREEN_ASH | VIOSCREEN_HEI_SODIUM | VIOSCREEN_SFA60 | |
| COUNTRY | PCR_PRIMERS | VIOSCREEN_ASPARTAM | VIOSCREEN_HEI_SOL_FAT_ALC_ADD_SUG | VIOSCREEN_SFA80 | |
| COUNTRY_OF_BIRTH | PD_whole_tree_10k | VIOSCREEN_ASPARTIC | VIOSCREEN_HEI_VEG | VIOSCREEN_SFATOT | |
| COUNTRY_RESIDENCE | PD_whole_tree_1k | VIOSCREEN_AVCARB | VIOSCREEN_HEI_WHL_GRAINS | VIOSCREEN_SUCPOLY | |
| CSECTION | PETS_OTHER | VIOSCREEN_BCODEID | VIOSCREEN_HISTIDIN | VIOSCREEN_SUCROLOSE | |
| DEODORANT_USE | PETS_OTHER_FREETEXT | VIOSCREEN_BETACAR | VIOSCREEN_INOSITOL | VIOSCREEN_SORBITOL | |
| DEPRESSION_BIPOLAR_SCHIZOPHRENIA | PHYSICAL_SPECIMEN_LOCATION | VIOSCREEN_BETACRYP | VIOSCREEN_IRON | VIOSCREEN_SRVID | |
| DEPTH | PHYSICAL_SPECIMEN_REMAINING | VIOSCREEN_BETAINE | VIOSCREEN_ISOLEUC | VIOSCREEN_STARCH | |
| Description | PKU | VIOSCREEN_BETATOCO | VIOSCREEN_ISOMALT | VIOSCREEN_STARTED | |
| DIABETES | PLATFORM | VIOSCREEN_BIOCHANA | VIOSCREEN_JOULES | VIOSCREEN_SUBJECT_ID | |
| DIABETES_TYPE | PLATING | VIOSCREEN_BMI | VIOSCREEN_JUICE_SERVINGS | VIOSCREEN_SUCPOLY | |
| DIET_TYPE | POOL_FREQUENCY | VIOSCREEN_CAFFEINE | VIOSCREEN_LACTITOL | VIOSCREEN_SUCROLOSE | |
| DNA_EXTRACTED | POULTRY_FREQUENCY | VIOSCREEN_CALCIUM | VIOSCREEN_LACTOSE | VIOSCREEN_SUCROSE | |
| DOG | PREGNANT | VIOSCREEN_CALCIUM_AVG | VIOSCREEN_LEGUMES | VIOSCREEN_SWEET_SERVINGS | |
| DOMINANT_HAND | PREPARED_MEALS_FREQUENCY | VIOSCREEN_CALCIUM_DOSE | VIOSCREEN_LEUCINE | VIOSCREEN_TAGATOSE | |
| DRINKING_WATER_SOURCE | PRIMER_DATE | VIOSCREEN_CALCIUM_FREQ | VIOSCREEN_LINE_GI | VIOSCREEN_TFA161T | |
| DRINKS_PER_SESSION | PRIMER_PLATE | VIOSCREEN_CALCIUM_FROM_DAIRY_SERVINGS | VIOSCREEN_LOW_FAT_DAIRY_SERVING | VIOSCREEN_TFA181T | |
| ECONOMIC_REGION | PROBIOTIC_FREQUENCY | VIOSCREEN_CALCIUM_SERVINGS | VIOSCREEN_LUTZEAX | VIOSCREEN_TFA182T | |
| ELEVATION | PROCESSING_ROBOT | VIOSCREEN_CALORIES | VIOSCREEN_LYCOPENE | VIOSCREEN_TGRAIN | |
| ENA-BASE-COUNT | PROJECT_NAME | VIOSCREEN_CARBO | VIOSCREEN_LYSINE | VIOSCREEN_THIAMIN | |
| ENA-CHECKLIST | PUBLIC | VIOSCREEN_CHOLEST | VIOSCREEN_MAGNES | VIOSCREEN_THREONIN | |
| ENA-SPOT-COUNT | QIITA_PREP_ID | VIOSCREEN_CHOLINE | VIOSCREEN_MALTITOL | VIOSCREEN_TIME | |
| ENV_BIOME | QIITA_STUDY_ID | VIOSCREEN_CLAC9T11 | VIOSCREEN_MALTOSE | VIOSCREEN_TOTALTFA | |
| ENV_FEATURE | RACE | VIOSCREEN_CLAT10C12 | VIOSCREEN_MANGAN | VIOSCREEN_TOTCLA | |
| ENV_MATERIAL | READY_TO_EAT_MEALS_FREQUENCY | VIOSCREEN_COPPER | VIOSCREEN_MANNITOL | VIOSCREEN_TOTFOLAT | |
| | | | | VIOSCREEN_TOTSUGAR | |

TABLE 4-continued

Potential Categories from which to Create Groups

| Categories1 | Categories2 | Categories3 | Categories4 | Categories5 | Categories6 |
|---|---|---|---|---|---|
| ENV_MATTER | RED_MEAT_FREQUENCY | VIOSCREEN_COUMEST | VIOSCREEN_M_EGG | VIOSCREEN_TRYPTOPH | |
| ENV_PACKAGE | REQUIRED_SAMPLE_INFO_STATUS | VIOSCREEN_CYSTINE | VIOSCREEN_METHHIS3 | VIOSCREEN_TYROSINE | |
| EPILEPSY_OR_SEIZURE_DISORDER | ROOMMATES | VIOSCREEN_DAIDZEIN | VIOSCREEN_METHION | VIOSCREEN_USER_ID | |
| EXERCISE_FREQUENCY | ROOMMATES_IN_STUDY | VIOSCREEN_DATABASE | VIOSCREEN_MFA141 | VIOSCREEN_VALINE | |
| EXERCISE_LOCATION | RUN_CENTER | VIOSCREEN_D_CHEESE | VIOSCREEN_MFA161 | VIOSCREEN_V_DRKGR | |
| EXPERIMENT_CENTER | RUN_DATE | VIOSCREEN_DELTTOCO | VIOSCREEN_MFA181 | VIOSCREEN_VEG5_DAY | |
| EXPERIMENT_DESIGN_DESCRIPTION | RUN_PREFIX | VIOSCREEN_DISCFAT_OIL | VIOSCREEN_MFA201 | VIOSCREEN_VEGETABLE_SERVINGS | |
| EXPERIMENT_TITLE | SALTED_SNACKS_FREQUENCY | VIOSCREEN_DISCFAT_SOL | VIOSCREEN_MFA221 | VIOSCREEN_VEGSUMM | |
| EXTRACTIONKIT_LOT | #Sample ID | VIOSCREEN_D_MILK | VIOSCREEN_MFATOT | VIOSCREEN_VISIT | |
| EXTRACTION_ROBOT | SAMPLE_PLATE | VIOSCREEN_DOB | VIOSCREEN_M_FISH_HI | VIOSCREEN_VITA_IU | |
| FED_AS_INFANT | SAMPLE_TYPE | VIOSCREEN_D_TOTAL | VIOSCREEN_M_FISH_LO | VIOSCREEN_VITA_RAE | |
| FERMENTED_PLANT_FREQUENCY | SAMP_SIZE | VIOSCREEN_D_TOT_SOYM | VIOSCREEN_M_FRANK | VIOSCREEN_VITA_RE | |

All scientific and technical terms used in this application have meanings commonly used in the art unless otherwise specified.

As used herein, the term "subject" includes humans and non-human animals. The term "non-human animal" includes all vertebrates, e.g., mammals and non-mammals, such as non-human primates, horses, sheep, dogs, cows, pigs, chickens, and other veterinary subjects and test animals.

The use of the singular can include the plural unless specifically stated otherwise. As used in the specification and the appended claims, the singular forms "a", "an", and "the" can include plural referents unless the context clearly dictates otherwise. The use of "or" can mean "and/or" unless stated otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

As used herein, the terms "sample" and "biological sample" refer to any sample suitable for the methods provided by the present invention. A sample of cells can be any sample, including, for example, gut or fecal sample obtained by non-invasive or invasive techniques such as biopsy of a subject. In one embodiment, the term "sample" refers to any preparation derived from fecal matter or gut tissue of a subject. For example, a sample of cells obtained using the non-invasive method described herein can be used to isolate nucleic acid molecules or proteins for the methods of the present invention.

In embodiments, analysis can be of any nucleic acid, including DNA, RNA, cDNA, miRNA, mtDNA, single or double-stranded. This nucleic acid can be of any length, as short as oligos of about 5 bp to as long a megabase or even longer. As used herein, the term "nucleic acid molecule" means DNA, RNA, single-stranded, double-stranded or triple stranded and any chemical modifications thereof. Virtually any modification of the nucleic acid is contemplated. A "nucleic acid molecule" can be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule. For methods that analyze expression of a gene, the nucleic acid isolated from a sample is typically RNA.

A single-stranded nucleic acid molecule is "complementary" to another single-stranded nucleic acid molecule when it can base-pair (hybridize) with all or a portion of the other nucleic acid molecule to form a double helix (double-stranded nucleic acid molecule), based on the ability of guanine (G) to base pair with cytosine (C) and adenine (A) to base pair with thymine (T) or uridine (U). For example, the nucleotide sequence 5'-TATAC-3' is complementary to the nucleotide sequence 5'-GTATA-3'.

As used herein "hybridization" refers to the process by which a nucleic acid strand joins with a complementary strand through base pairing. Hybridization reactions can be sensitive and selective so that a particular sequence of interest can be identified even in samples in which it is present at low concentrations. In an in vitro situation, suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature. For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 mg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

As used herein, the term "microbiome" refers to microorganisms, including bacteria, viruses, and fungi, archaea, protozoa, amoeba, or helminths that inhabit the gut of the subject.

As used herein, the terms microbial, microbe, or microorganism refer to any microscopic organism including prokaryotes or eukaryotes, spores, bacterium, archeaebacterium, fungus, virus, or protist, unicellular or multicellular.

The present invention is described partly in terms of functional components and various processing steps. Such functional components and processing steps may be realized by any number of components, operations and techniques configured to perform the specified functions and achieve the various results. For example, the present invention may employ various biological samples, biomarkers, elements, materials, computers, data sources, storage systems and media, information gathering techniques and processes, data processing criteria, statistical analyses, regression analyses and the like, which may carry out a variety of functions. In addition, although the invention is described in the medical diagnosis context, the present invention may be practiced in conjunction with any number of applications, environments and data analyses; the systems described herein are merely exemplary applications for the invention.

Methods for data analysis according to various aspects of the present invention may be implemented in any suitable manner, for example using a computer program operating on the computer system. An exemplary analysis system, according to various aspects of the present invention, may be implemented in conjunction with a computer system, for example a conventional computer system comprising a processor and a random access memory, such as a remotely-accessible application server, network server, personal computer or workstation. The computer system also suitably includes additional memory devices or information storage systems, such as a mass storage system and a user interface, for example a conventional monitor, keyboard and tracking device. The computer system may, however, comprise any suitable computer system and associated equipment and may be configured in any suitable manner. In one embodiment, the computer system comprises a stand-alone system. In another embodiment, the computer system is part of a network of computers including a server and a database.

The software required for receiving, processing, and analyzing genetic information may be implemented in a single device or implemented in a plurality of devices. The software may be accessible via a network such that storage and processing of information takes place remotely with respect to users. The analysis system according to various aspects of the present invention and its various elements provide functions and operations to facilitate microbiome analysis, such as data gathering, processing, analysis, reporting and/or diagnosis. The present analysis system maintains information relating to microbiomes and samples and facilitates analysis and/or diagnosis. For example, in the present embodiment, the computer system executes the computer program, which may receive, store, search, analyze, and report information relating to the microbiome. The computer program may comprise multiple modules performing various functions or operations, such as a processing module for processing raw data and generating supplemental data and an analysis module for analyzing raw data and supplemental data to generate a models and/or predictions.

The analysis system may also provide various additional modules and/or individual functions. For example, the analysis system may also include a reporting function, for example to provide information relating to the processing and analysis functions. The analysis system may also provide various administrative and management functions, such as controlling access and performing other administrative functions.

To the extent necessary to understand or complete the disclosure of the present invention, all publications, patents, and patent applications mentioned herein are expressly incorporated by reference therein to the same extent as though each were individually so incorporated.

Although the invention has been described with reference to the above example, it will be understood that modifications and variations are encompassed within the spirit and scope of the invention. Accordingly, the invention is limited only by the following claims.

What is claimed is:

1. A method for preparing and analyzing a sample comprising:
   a) extracting genetic material from a diverse population of microbes present in a first sample obtained from a subject using one or more of a detergent, a chelator, a glucoside hydrolase and a chaotropic agent and performing whole genome sequencing of DNA from the extracted genetic material,
   wherein the diverse population of microbes comprises two or more microbes selected from the group consisting of bacteria, archaea, fungi, protozoa, helminths, parasites, viruses, phages, spores, and algae;
   b) subjecting the extracted genetic material from the first sample to metagenomics analysis and quality filtering before taxonomy assignment;
   c) measuring a diversity number for the first sample relative to an average diversity number and generating a microbiome score indicative of relative abundances of different types of microbes present in the first sample;
   d) diagnosing the subject as having or at risk of having dysbiosis based on the metagenomics analysis of the first sample;
   e) preparing and administering to the subject diagnosed as having or at risk of having dysbiosis, a customized probiotic, prebiotic, enzyme, vitamin supplement, mineral supplement, dietary supplement and/or botanical mixture which is formulated specifically to treat the dysbiosis in the subject and based on the metagenomics analysis and the microbiome score generated for the subject;
   f) extracting genetic material from a diverse population of microbes present in a second sample obtained from the subject following the administering of e) in the same manner as the extraction of genetic material from the first sample in a);
   g) performing metagenomics analysis on the extracted genetic material from the second sample and quality filtering before taxonomy assignment;
   h) assessing the effectiveness of the dysbiosis treatment; and
   i) administering to the subject a second customized probiotic, prebiotic, enzyme, vitamin supplement, mineral supplement, dietary supplement and/or botanical mixture which is formulated specifically to the dysbiosis in the subject and based on the assessment of effectiveness to treat the dysbiosis.

2. The method of claim 1, further comprising performing sequencing of RNA from the extracted genetic material.

3. The method of claim 1, wherein extracting genetic material comprises magnetic bead based nucleic acid purification.

4. The method of claim 1, wherein extracting genetic material comprises phenol-chloroform-alcohol extraction.

5. The method of claim 1, wherein extracting genetic material comprises a heat shock treatment.

6. The method of claim 1, wherein extracting genetic material comprises treatment of the sample to induce germination of bacterial spores and/or fungal spores present in the sample.

7. The method of claim 1, further comprising inducing physical lysis of cells by mechanical treatment of the sample in a).

8. The method of claim 7, wherein mechanical treatment comprises sonication, bead mixing, bead mill homogenization, pressurization, microfluidization, or any combination thereof.

9. The method of claim 1, wherein the first and second samples are obtained from a gut of the subject.

10. The method of claim 1, comprising identifying one or more food stuffs the subject has consumed and/or one or more macronutrients the subject has consumed based on a food DNA sequence from the extracted genetic material.

11. The method of claim 1, further comprising determining a dietary guidance for the subject based on the metagenomics analysis.

12. The method of claim 11, further comprising treating the subject with a food stuff based on the dietary guidance.

13. The method of claim 1, further comprising identifying of a disease or disorder based on the dysbiosis.

14. The method of claim 1, comprising determining metabolomic data from the metagenomics analysis or determining a functional metagenomic analysis of the first or second sample by testing for metabolites.

15. The method of claim 1, comprising performing metagenomics analysis by preprocessing of sequencing information selected from removing duplicates, removing adaptor sequencing, removing 5' or 3' sequencing to improve the quality of base calling, including only base calls of a particular quality, filtering human reads, creating paired reads or separating them, and limiting overlap of reads.

16. The method of claim 1, comprising performing metagenomics analysis by aligning sequencing information to a database by use of a software or system where the sequencing information may be broken into k-mers of particular length, used as full fragments, be scaffolded and aligned to a large reference genome, or other method to create a report of organisms identified, relative abundance of organism identified, genome size, total fragments aligned, unique fragments aligned at the strain, species, genus, family, order, class, phylum, kingdom, or domain.

17. The method of claim 1, further comprising monitoring the subject following treatment with the customized probiotic, prebiotic, enzyme, vitamin supplement, mineral supplement, dietary supplement and/or botanical mixture.

* * * * *